United States Patent
Iinuma et al.

(10) Patent No.: US 9,428,477 B2
(45) Date of Patent: Aug. 30, 2016

(54) TRANS-2-DECENOIC ACID DERIVATIVE AND DRUG CONTAINING SAME

(71) Applicants: NIPPON ZOKI PHARMACEUTICAL CO., LTD., Osaka-shi, Osaka (JP); NAGOYA INDUSTRIAL SCIENCE RESEARCH INSTITUTE, Nagoya-shi, Aichi (JP)

(72) Inventors: Munekazu Iinuma, Gifu (JP); Shoei Furukawa, Gifu (JP); Mitsuru Naiki, Kato (JP); Tomonori Matsumoto, Kato (JP); Kunihiko Higashiura, Kato (JP)

(73) Assignees: NIPPON ZOKI PHARMACEUTICAL CO., LTD., Osaka (JP); NAGOYA INDUSTRIAL SCIENCE RESEARCH INSTITUTE, Nagoya (JP)

( * ) Notice: Subject to any disclaimer, the term of this patent is extended or adjusted under 35 U.S.C. 154(b) by 74 days.

(21) Appl. No.: 14/395,241

(22) PCT Filed: Apr. 26, 2013

(86) PCT No.: PCT/JP2013/062373
§ 371 (c)(1),
(2) Date: Oct. 17, 2014

(87) PCT Pub. No.: WO2013/161993
PCT Pub. Date: Oct. 31, 2013

(65) Prior Publication Data
US 2015/0087823 A1    Mar. 26, 2015

(30) Foreign Application Priority Data

Apr. 27, 2012 (JP) ................................ 2012-103306

(51) Int. Cl.
| | | |
|---|---|---|
| C07D 207/08 | (2006.01) |
| C07D 295/185 | (2006.01) |
| C07D 213/74 | (2006.01) |
| C07D 239/42 | (2006.01) |
| C07D 243/08 | (2006.01) |
| C07D 207/16 | (2006.01) |
| C07D 277/04 | (2006.01) |
| C07D 211/16 | (2006.01) |

(Continued)

(52) U.S. Cl.
CPC ......... *C07D 295/185* (2013.01); *C07D 207/16* (2013.01); *C07D 211/16* (2013.01); *C07D 211/18* (2013.01); *C07D 211/26* (2013.01); *C07D 211/30* (2013.01); *C07D 211/44* (2013.01); *C07D 211/46* (2013.01); *C07D 211/48* (2013.01); *C07D 211/58* (2013.01); *C07D 211/62* (2013.01); *C07D 211/74* (2013.01); *C07D 213/74* (2013.01); *C07D 239/42* (2013.01); *C07D 243/08* (2013.01); *C07D 277/04* (2013.01); *C07D 295/18* (2013.01); *C07D 207/08* (2013.01)

(58) Field of Classification Search
CPC ............ C07D 213/74; C07D 295/185; C07D 243/08; C07D 207/16; C07D 277/04; C07D 211/16; C07D 211/18; C07D 211/26; C07D 211/30; C07D 211/44; C07D 211/46; C07D 211/48; C07D 211/58; C07D 211/62; C07D 295/18; C07D 211/74
See application file for complete search history.

(56) References Cited

U.S. PATENT DOCUMENTS

| 3,294,794 A | 12/1966 | Holmes et al. |
| 8,466,192 B2 * | 6/2013 | Huang ................... A01N 37/02 504/287 |

(Continued)

FOREIGN PATENT DOCUMENTS

| RU | 2227794 C2 | 4/2004 |
| WO | 2009/038110 A1 | 3/2009 |

(Continued)

OTHER PUBLICATIONS

H. Huang et al., 58 Journal of Agricultural and Food Chemistry, 9994-10000 (2010).*

(Continued)

*Primary Examiner* — Alexander R Pagano
(74) *Attorney, Agent, or Firm* — Oliff PLC

(57) ABSTRACT

The present invention relates to a novel trans-2-decenoic acid derivative or a pharmaceutically acceptable salt thereof, and a pharmaceutical agent containing the compound as an active ingredient. The trans-2-decenoic acid derivative or a pharmaceutically acceptable salt, which is the compound of the present invention, is specifically represented by the general formula (I):

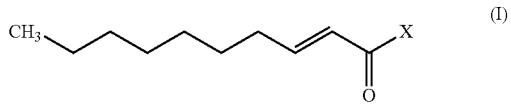

wherein X is a substituent such as a 1-pyrrolidyl, a 3-thiazolizyl, or a piperidino, and the compound is highly useful as a pharmaceutical agent, such as a prophylactic or therapeutic agent for a peripheral nerve disorder induced by administration of an anticancer agent, a prophylactic or therapeutic agent for neurodegenerative diseases or mental diseases such as dementia, Alzheimer's disease, Parkinson's disease, diabetic neuropathy, depression, glaucoma, or autistic disorder spectrum, a therapeutic or repairing agent for spinal cord injury, analgesics against various pain diseases, or the like.

8 Claims, No Drawings

(51) Int. Cl.
*C07D 211/18* (2006.01)
*C07D 211/26* (2006.01)
*C07D 211/30* (2006.01)
*C07D 211/44* (2006.01)
*C07D 211/46* (2006.01)
*C07D 211/48* (2006.01)
*C07D 211/58* (2006.01)
*C07D 211/62* (2006.01)
*C07D 295/18* (2006.01)
*C07D 211/74* (2006.01)

(56) References Cited

U.S. PATENT DOCUMENTS

| | | | | |
|---|---|---|---|---|
| 8,883,791 B2* | 11/2014 | Berger | ............... | C07D 401/04 514/252.16 |
| 8,957,000 B2* | 2/2015 | Huang | ............... | A01N 37/02 504/220 |
| 8,968,723 B2* | 3/2015 | Asolkar | ............... | A01N 37/18 424/93.47 |
| 9,179,675 B2* | 11/2015 | Huang | ............... | A01N 37/02 |
| 9,259,446 B2* | 2/2016 | Asolkar | ............... | A01N 37/18 |
| 2003/0153544 A1 | 8/2003 | Myhren et al. | | |
| 2004/0034242 A1* | 2/2004 | Yang | ............... | C07C 39/08 554/9 |
| 2005/0075368 A1* | 4/2005 | Dewis | ............... | A01N 37/18 514/330 |
| 2010/0266717 A1* | 10/2010 | Asolkar | ............... | A01N 37/18 424/780 |
| 2011/0021358 A1* | 1/2011 | Huang | ............... | A01N 37/02 504/220 |
| 2013/0196013 A1* | 8/2013 | Asolkar | ............ | C07D 295/185 424/780 |
| 2013/0203768 A1* | 8/2013 | Berger | ............... | C07D 401/04 514/252.16 |
| 2013/0225837 A1 | 8/2013 | Iinuma et al. | | |

FOREIGN PATENT DOCUMENTS

| | | | |
|---|---|---|---|
| WO | 2010/123894 A2 | 10/2010 | |
| WO | WO 2011011415 A2 * | 1/2011 | ............ A01N 37/02 |
| WO | 2011/093512 A1 | 8/2011 | |
| WO | 2012/060396 A1 | 5/2012 | |

OTHER PUBLICATIONS

Nov. 17, 2015 Extended Search Report issued in European Patent Application No. 13781244.2.
Ley et al., "Structure-activity relationships of trigeminal effects for artificial and natural occuring alkamides related to spilanthol," 2006, Flavour Science, pp. 21-24.
Choi et al., "Piperine protects cisplatin-induced apoptosis via heme oxygenase-1 induction in auditory cells," Journal of Nutritional Biochemistry, 2007, vol. 18, pp. 615-622.
Bang et al., "Anti-inflammatory and antiarthritic effects of piperine in human interleukin 1b-stimulated fibroblast-like synoviocytes and in rat arthritis models," Arthritis Research & Therapy, 2009, vol. 11, No. 2, pp. 1-9.
Li et al., "Antidepressant like effects of piperine in chronic mild stress treated mice and its possible mechanisms," Life Sciences, 2007, vol. 80, pp. 1373-1381.
Journal of Economic Entomology, 1970, vol. 63, No. 6, pp. 1752-1755.
Jul. 23, 2013 International Search Report issued in International Application No. PCT/JP2013/062373.
Oct. 28, 2014 International Preliminary Report on Patentability issued in International Application No. PCT/JP2013/062373.
Jan. 26, 2016 Russian Office Action issued in Russian Patent Application No. 2014147728/04.

* cited by examiner

TRANS-2-DECENOIC ACID DERIVATIVE AND DRUG CONTAINING SAME

TECHNICAL FIELD

The present invention relates to a novel trans-2-decenoic acid derivative or a pharmaceutically acceptable salt thereof, and a pharmaceutical agent containing the compound (in the present invention, in a case where it is simply referred to as a "compound," it may include a pharmaceutically acceptable salt thereof) as an active ingredient. More specifically, the present invention relates to a trans-2-decenoic acid derivative or a pharmaceutically acceptable salt thereof, having prophylactic or therapeutic actions for peripheral nerve disorders induced by administration of anti-cancer agents, neurotrophic factor-like activity such as nerve growth factor (NGF) or brain-derived neurotrophic factor (BDNF), and a pharmacological action such as analgesic action, and a pharmaceutical agent containing the compound as an active ingredient.

BACKGROUND ART

To date, in cancer (malignant tumor) treatment, surgery, irradiation or chemotherapy is used alone or in any combination thereof as required. Among them, anti-cancer agents (anti-malignant-tumor agents) used in the chemotherapy inherently have cytotoxicity and damage not only the cancer cells but also human normal cells to cause side effects. Thus, it is important that the anti-cancer agents are administered to patients so as to prevent or treat such side effects as far as possible and to provide sufficient anti-cancer effects.

Examples of the side effects induced by administration of anti-cancer agents include variously blood disorders, gastrointestinal disorders, nerve disorders, etc. and, in particular, acute or chronic nerve disorders have increased as a recent trend. This trend is considered to be caused by the following factors: frequent occurrence of nerve disorders as a main side effect of new anti-cancer agents providing remarkable anticancer effects, the effects of multiple drug therapy as recent main therapy, and a relatively improved tendency of side effects such as blood disorders and gastrointestinal disorders. In this manner, no effective countermeasures against the nerve disorders, which are a main side effect caused by the current cancer chemotherapy, are available once the disorders have developed, due to the difficulty of nerve cell regeneration. Therefore, serious symptoms or irreversible disorders may be developed so that the administration of anti-cancer agents cannot be continued in some cases. Accordingly, the nerve disorders are an important therapeutic problem for cancer.

The nerve disorders induced by administration of anti-cancer agents are observed in, besides the central nervous system, the autonomic nervous system, and the peripheral nervous system, the sense organs such as the sense of taste. Among them, nerve disorders in the peripheral nervous system that occur in a comparatively high frequency to be problems are pains such as a stinging pain and burning pain, paresthesia such as numbness of limb extremities and a burning sensation, hyperesthesia such as hypersensitivity to cold stimuli, dysesthesia such as sensory loss, sensory paralysis and sense of discomfort, sensory ataxia, muscle weakness or the like. In the present invention the anti-cancer agent inducing the peripheral nerve disorder may be any kinds of them, and the lesions in the peripheral nervous system induced by administration of anti-cancer agents are considered to be mainly due to neuroaxonal degeneration.

Microtubules in the axon play an important role in maintaining the normal function of cells, for example, forming a spindle during cell division, and involving in placing the subcellular organelle and transporting substances. A taxane drug such as paclitaxel and docetaxel and a vinca alkaloid drug such as vincristine, vinblastine, vindesine and vinorelbine target the microtubules to inhibit the proliferation of cancer cells. Thus, it is considered that the microtubules in normal nerve cells are also more likely to be damaged to cause nerve disorders. Furthermore, it is considered that a platinum drug such as oxaliplatin, carboplatin, cisplatin and nedaplatin directly damage nerve cells, and consequently secondarily leading to axonopathy, so that it is considered to cause much of the nerve disorders.

In spite of the above situation, the neurotoxicity of the anti-cancer agents has not been studied in detail and sufficient prophylactic and therapeutic methods for the peripheral nerve disorder which is a side effect caused by taxane anti-cancer drugs, etc. as described above have yet to be established. Therefore, at present, for relieving numbness symptoms, vitamin $B_{12}$ preparations such as mecobalamin and a Chinese herbal medicine, Gosha-jinki-gan, are used. For pains, an antidepressant (amitriptyline hydrochloride), an antiepileptic agent (carbamazepine), an antiarrhythmic agent (mexiletine hydrochloride), adrenocorticosteroid and the like are used. However, these therapies have limited effectiveness. Stopping the administration of anti-cancer agent is the only reliable method for preventing the development of the peripheral nerve disorder, but even after stopping the administration, the peripheral nerve disorder may continue or get worse. It would require the administration of anti-cancer agents for treatment of cancer, but a significant peripheral nerve disorder can make it difficult to continue the administration of important anti-cancer agents which are highly effective against cancer and it becomes a serious problem for treatment of cancer. In view of the above problems, more effective prophylactic or therapeutic agents against a peripheral nerve disorder induced by anti-cancer agents have been strongly required in clinical practices.

In addition, a nerve cell is a cell having an information transmitting function, and its damage emerges as a serious loss of a cranial nerve function. The regeneration of the axon can hardly be expected in central nerves of the brain and the spinal cords, and thus, when nerve cells are found to have damages or degeneration, it is necessary to protect and activate the nerve cells. As the biological protective mechanism mentioned above, the roles of neurotrophic factors in differentiation of nerve cells, survival sustenance, increase in synapse functions, and regeneration or repair of the damaged nerve axon are indispensable.

Among neurotrophic factors, a nervous growth factor (NGF), a brain-derived neurotrophic factor (BDNF), neurotrophin-3 (NT-3), neurotrophin-4/5 (NT-4/5), and the like construct a neurotrophin family having 50% or more of sequence homology with NGF as a prototype. When the extracellularly secreted neurotrophin is bound to high-affinity receptor (Trks) on a nerve cell membrane, signals are transmitted in three directions in the nerve cells. A transcription factor CREB (cAMP-response element binding protein) is activated through the activation of MAP kinase (mitogen-activated protein (MAP) kinases/extracellular signal-regulated protein kinases 1/2 (ERK1/2)) information transmission pathway, including the activation (phosphorylation) of the MAP kinase, which is one of the high-affinity receptors, thereby regulating numerous gene expressions. Therefore, once signal transmissions through a MAP kinase information transmission pathway can be activated, there is a possibility of clinical applications to a nervous disorder caused by degeneration of nerve cells or cellular death. Further, there is a report about associations between BDNF and some diseases.

According to the studies on gene polymorphisms of BDNF, it is reported that particular polymorphisms of the BDNF are associated with Parkinson's disease, Alzheimer's disease, depression, bipolar depression, anxiety disorders, autistic disorder spectrum, glaucoma, and the like. Furthermore, there are some reports that decrease in a synapse function of a genetically converted mouse having Huntington's disease is cured with administration of a BDNF, and that administration of a MAP kinase phosphorylation inhibitor provokes an antidepressant condition.

Neurotrophic factors, as is seen in examples of BDNF mentioned above, show therapeutic effects against particular nerve diseases, and have some actions of germinating the axon and extending its length. However, since neurotrophic factors are high-molecular weight proteins, they have a problem of having difficulty in reaching the brain since they cannot pass through a blood-brain barrier even if administered from a peripheral. Thus, it has been tried to search for a pharmaceutical agent having a neurotrophic factor-like activity that activates nerve cells with a low-molecular weight compound and a pharmaceutical agent promoting the production and secretion of neurotrophic factors.

Patent Publication 1 discloses that a fatty acid or a fatty acid ester having 8 carbon atoms or 10 to 12 carbon atoms has a neutrophic factor-like activity. However, the compounds described in Patent Publication 1 is an ordinary fatty acid or an ester thereof, clearly differing in the structure in the carboxylic acid moiety from the compounds of the present invention. In addition, the compounds of the present invention, 1-((E)-2-decenoyl)pyrrolidine (Compound 1), 1-((E)-2-decenoyl)piperidine (Compound 5) and 1-((E)-2-decenoyl)azepane (Compound 32), are disclosed in Patent Publication 2, and the compound of the present invention, (4-((E)-2-decenoyl) morpholine (Compound 17), is disclosed in Patent Publication 3 or Non-Patent Publication 1, respectively. However, Patent Publication 2 relates to a toxic action against molluskans, and Patent Publication 3 relates to growth inhibitory actions against disease germs or molds, and Non-Patent Publication 1 is a publication relating to a repellant against houseflies. In conclusion, none of these publications include pharmaceutical applications of the compounds of the present invention and any descriptions suggesting the applications.

PRIOR ART REFERENCES

Patent Publications

Patent Publication 1: WO 2009/038110
Patent Publication 2: WO 2010/123894
Patent Publication 3: U.S. Pat. No. 3,294,794

Non-Patent Publications

Non-Patent Publication 1: *Journal of Economic Entomology*, 1970, 63(6), 1752-1755

SUMMARY OF THE INVENTION

Problems to be Solved by the Invention

An object of the present invention is to provide a novel trans-2-decenoic acid derivative or a pharmaceutically acceptable salt thereof, and a pharmaceutical agent containing the compound as an active ingredient, and more specifically to provide a pharmaceutical agent having a prophylactic or therapeutic action against a peripheral nerve disorder induced by an anti-cancer agent, a neurotrophic factor-like activity or a pharmacological action such as analgesic action, wherein in the present invention, the "peripheral nerve disorder" can be replaced with a synonym "neuropathy"; in addition, "prevention" and "treatment" include "improvement" or "alleviation," and "prophylactic agent" and "therapeutic agent" include "improvement agent" or "alleviating agent."

Means to Solve the Problems

As a result of intensively studies in order to solve the above problems, the present inventors have found that a trans-2-decenoic acid derivative represented by the general formula (I) defined below or a pharmaceutically acceptable salt thereof has an excellent pharmacological action such as a prophylactic or therapeutic action for peripheral nerve disorders induced by anti-cancer agents, a neurotrophic factor-like activity, or an analgesic action. The present inventors have made further studies on the basis of the above findings, and whereby the present invention has been accomplished.

Specifically, the present invention provides the following compounds and pharmaceutical agents containing the compounds.

(1) A trans-2-decenoic acid derivative represented by the following general formula (I') or a pharmaceutically acceptable salt thereof:

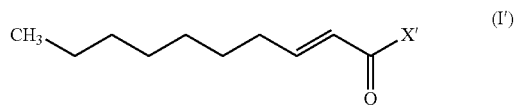

wherein X' is:
(a) a 1-pyrrolidyl substituted with carboxyl or alkoxycarbonyl,
(b) a 3-thiazolidyl,
(c) a piperidino substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl,
(d) a thiomorpholino,
(e) a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl,
(f) a 1-piperazyl substituted with a phenyl which may be substituted with alkylamino, halogen, alkoxy, alkyl, hydroxy, carboxyalkoxy or alkoxycarbonylalkoxy,
(g) a 1,4-diazepanyl which may be substituted with alkyl or alkylaminoalkyl, or
(h) a carboxymorpholino.

(2) The trans-2-decenoic acid derivative or a pharmaceutically acceptable salt thereof according to the above (1), wherein X' is a 1-pyrrolidyl substituted with carboxyl or alkoxycarbonyl.

(3) The trans-2-decenoic acid derivative or a pharmaceutically acceptable salt thereof according to the above (1), wherein X' is a 3-thiazolidyl.

(4) The trans-2-decenoic acid derivative or a pharmaceutically acceptable salt thereof according to the above (1), wherein X' is a piperidino substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano or halogenophenyl.

(5) The trans-2-decenoic acid derivative or a pharmaceutically acceptable salt thereof according to the above (1), wherein X' is a thiomorpholino.

(6) The trans-2-decenoic acid derivative or a pharmaceutically acceptable salt thereof according to the above (1), wherein X' is a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl.

(7) The trans-2-decenoic acid derivative or a pharmaceutically acceptable salt thereof according to the above (1), wherein X' is a 1-piperazyl substituted with a phenyl which may be substituted with alkylamino, halogen, alkoxy, alkyl, hydroxy, carboxyalkoxy or alkoxycarbonylalkoxy.

(8) The trans-2-decenoic acid derivative or a pharmaceutically acceptable salt thereof according to the above (1), wherein X' is a 1,4-diazepanyl which may be substituted with alkyl or alkylaminoalkyl.

(9) The trans-2-decenoic acid derivative or a pharmaceutically acceptable salt thereof according to the above (1), wherein X' is a carboxymorpholino.

(10) A pharmaceutical agent containing, as an active ingredient, at least one member of a trans-2-decenoic acid derivative represented by the following general formula (I) and a pharmaceutically acceptable salt thereof:

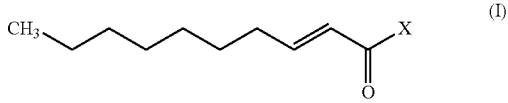

wherein X is:
(a) a 1-pyrrolidyl which may be substituted with carboxyl or alkoxycarbonyl,
(b) a 3-thiazolidyl,
(c) a piperidino which may be substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl,
(d) a morpholino,
(e) a thiomorpholino which may be substituted with carboxyl,
(f) a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl,
(g) a 1-piperazyl substituted with a phenyl which is substituted with alkylamino, halogen, alkoxy, alkyl, hydroxy, carboxyalkoxy or alkoxycarbonylalkoxy,
(h) a 1-azepanyl, or
(i) a 1,4-diazepanyl which may be substituted with alkyl or alkylaminoalkyl.

(11) The pharmaceutical agent according to the above (10), wherein X is a 1-pyrrolidyl which may be substituted with carboxyl or alkoxycarbonyl.

(12) The pharmaceutical agent according to the above (10), wherein X is a 3-thiazolidyl.

(13) The pharmaceutical agent according to the above (10), wherein X is a piperidino which may be substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl.

(14) The pharmaceutical agent according to the above (10), wherein X is a morpholino which may be substituted with carboxyl.

(15) The pharmaceutical agent according to the above (10), wherein X is a thiomorpholino.

(16) The pharmaceutical agent according to the above (10), wherein X is a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl.

(17) The pharmaceutical agent according to the above (10), wherein X is a 1-piperazyl substituted with a phenyl which may be substituted with alkylamino, halogen, alkoxy, alkyl, hydroxy, carboxyalkoxy or alkoxycarbonylalkoxy.

(18) The pharmaceutical agent according to the above (10), wherein X is a 1-azepanyl.

(19) The pharmaceutical agent according to the above (10), wherein X is a 1,4-diazepanyl which may be substituted with alkyl or alkylaminoalkyl.

(20) The pharmaceutical agent according to any one of the above (10) to (19), wherein the pharmaceutical agent is a prophylactic agent or therapeutic agent for peripheral nerve disorders induced by administration of a drug containing at least one anti-cancer agent.

(21) The pharmaceutical agent according to the above (20), wherein the anti-cancer agent is a microtubule inhibitor.

(22) The pharmaceutical agent according to the above (21), wherein the microtubule inhibitor is a taxane drug.

(23) The pharmaceutical agent according to the above (22), wherein the taxane drug is paclitaxel or docetaxel.

(24) The pharmaceutical agent according to the above (23), wherein the taxane drug is paclitaxel.

(25) The pharmaceutical agent according to the above (21), wherein the microtubule inhibitor is a vinca alkaloid drug.

(26) The pharmaceutical agent according to the above (25), wherein the vinca alkaloid drug is vincristine.

(27) The pharmaceutical agent according to the above (20), wherein the anti-cancer agent is a platinum drug.

(28) The pharmaceutical agent according to the above (27), wherein the platinum drug is oxaliplatin or cisplatin.

(29) The pharmaceutical agent according to any one of the above (20) to (28), wherein the peripheral nerve disorders induced by an anti-cancer agent are an acute or chronic pain, numbness, paresthesia, hyperesthesia, or dysesthesia.

(30) The pharmaceutical agent according to any one of the above (10) to (19), wherein the pharmaceutical agent is an agent having neutrophic factor-like activity.

(31) The pharmaceutical agent according to the above (30), wherein the agent having neutrophic factor-like activity is a prophylactic or therapeutic agent for neurodegenerative diseases or mental diseases.

(32) The pharmaceutical agent according to the above (31), wherein the agent having neutrophic factor-like activity is a prophylactic or therapeutic agent for neurodegenerative diseases.

(33) The pharmaceutical agent according to the above (32), wherein the neurodegenerative disease is dementia, Alzheimer's disease, Parkinson's disease, amyotrophic lateral sclerosis (ALS), Huntington's disease, progressive supranuclear palsy (PSP), diabetic neuropathy, or glaucoma.

(34) The pharmaceutical agent according to the above (31), wherein the agent having neutrophic factor-like activity is a prophylactic or therapeutic agent for mental diseases.

(35) The pharmaceutical agent according to the above (34), wherein the mental diseases are depression, anxiety disorders (neuroses), or autistic disorder spectrum.

(36) The pharmaceutical agent according to any one of the above (10) to (19), wherein the pharmaceutical agent is a therapeutic agent or repairing agent for spinal cord injury.

(37) The pharmaceutical agent according to any one of the above (10) to (19), wherein the pharmaceutical agent is an analgesic against pain diseases.

(38) The pharmaceutical agent according to the above (37), wherein the analgesic against the pain diseases is a therapeutic agent against arthralgia.

(39) The pharmaceutical agent according to the above (38), wherein the arthralgia is a pain induced by osteoarthritis.

(40) The pharmaceutical agent according to the above (39), wherein the osteoarthritis is knee osteoarthritis or hip osteoarthritis.

(41) The pharmaceutical agent according to any one of the above (10) to (40), wherein the pharmaceutical agent is an injectable preparation.

(42) The pharmaceutical agent according to any one of the above (10) to (40), wherein the pharmaceutical agent is an oral preparation.

(43) The pharmaceutical agent according to the above (41) or (42), wherein the injectable preparation or the oral preparation is a cyclodextrin inclusion complex.

(44) The pharmaceutical agent according to any one of the above (10) to (40), wherein the pharmaceutical agent is an external preparation.

(45) The pharmaceutical agent according to the above (44), wherein the external preparation is a patch preparation.

(46) A compound or a pharmaceutically acceptable salt thereof as defined in any one of the above (10) to (19), for use in the prevention or treatment of a disease as defined in any one of the above (20) to (29) and (31) to (40).

(47) A compound or a pharmaceutically acceptable salt thereof as defined in any one of the above (10) to (19), for use in the prevention or treatment of peripheral nerve disorders induced by administration of a drug containing at least one anti-cancer agent.

(48) A compound or a pharmaceutically acceptable salt thereof as defined in any one of the above (10) to (19), for use in the prevention or treatment of a neurodegenerative disease or a mental disease.

(49) A compound or a pharmaceutically acceptable salt thereof as defined in any one of the above (10) to (19), for use in the prevention or treatment of a pain disease.

(50) A method for preventing or treating a disease as defined in any one of the above (20) to (29) and (31) to (40), characterized in that the method includes administering the compound or a pharmaceutically acceptable salt thereof as defined in any one of the above (10) to (19) in an effective amount to a patient with the disease as defined in any one of the above (20) to (29) and (31) to (40).

(51) A method for preventing or treating a peripheral nerve disorder induced by administration of a drug containing at least one anti-cancer agent, characterized in that the method includes administering the compound or a pharmaceutically acceptable salt thereof as defined in any one of the above (10) to (19) in an effective amount to a patient with the peripheral nerve disorder induced by administration of a drug containing at least one anti-cancer agent.

(52) A method for preventing or treating a neurodegenerative disease or a mental disease, characterized in that the method includes administering the compound or a pharmaceutically acceptable salt thereof as defined in any one of the above (10) to (19) in an effective amount to a patient with a neurodegenerative disease or a mental disease.

(53) A method for preventing or treating a pain disease, characterized in that the method includes administering the compound or a pharmaceutically acceptable salt thereof as defined in any one of the above (10) to (19) in an effective amount to a patient with a pain disease.

(54) Use of a compound or a pharmaceutically acceptable salt thereof as defined in any one of the above (10) to (19) in the manufacture of a pharmaceutical agent for treatment of the disease as defined in any one of the above (20) to (29) and (31) to (40).

(55) Use of a compound or a pharmaceutically acceptable salt thereof as defined in any one of the above (10) to (19) in the manufacture of a pharmaceutical agent for prevention or treatment of a peripheral nerve disorder induced by administration of a drug containing at least one anti-cancer agent.

(56) Use of a compound or a pharmaceutically acceptable salt thereof as defined in any one of the above (10) to (19) in the manufacture of a pharmaceutical agent for prevention or treatment of a neurodegenerative disease or a mental disease.

(57) Use of a compound or a pharmaceutically acceptable salt thereof as defined in any one of the above (10) to (19) in the manufacture of an analgesic.

Effects of the Invention

The compound of the present invention is effective as a drug for prevention or treatment of nerve disorders of the peripheral nerve system induced by anti-cancer agents such as paresthesia such as numbness of limb extremities of human and animals, and hyperalgesia such as pains.

In addition, the compound of the present invention has an excellent neutrophic factor-like activity, so that the compound is usable as an agent having a neurotrophic factor-like activity. This agent having a neurotrophic factor-like activity is useful as prophylactic agents or therapeutic agents for nerve disorders because signal transmissions are activated via MAP kinase information transmission pathway with a neurotrophic factor-like activity. Among the nerve disorders, the agent is especially useful as prophylactic agents or therapeutic agents for a neurodegenerative disease, such as dementia, Alzheimer's disease, Parkinson's disease, amyotrophic lateral sclerosis (ALS), Huntington's disease, progressive supranuclear palsy (PSP), diabetic neuropathy, or glaucoma. In addition, among the nerve disorders, the agent is also useful as an improving agent for prevention of a mental disease. Among the mental diseases, the agent is especially useful as prophylactic agents or improving agents for depression, anxiety disorders (neuroses), or autistic disorder spectrum, and particularly useful as prophylactic agents or therapeutic agents for depression and anxiety disorders (neuroses).

In addition, the compound of the present invention is useful as a therapeutic agent for spinal cord injury (in the case of spinal cord injury, it is sometimes called as "repairing agent").

Further, the compound of the present invention is a compound showing an excellent analgesic action, which is useful as a drug for prevention or treatment of various pain diseases such as pains caused by arthralgia such as orthoarthritis.

MODES FOR CARRYING OUT THE INVENTION

The present invention relates to a trans-2-decenoic acid derivative represented by the following general formula (I') or a pharmaceutically acceptable salt thereof:

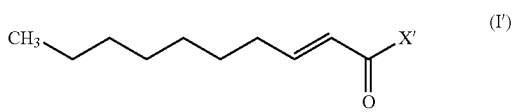

wherein X' is:
(a) a 1-pyrrolidyl substituted with carboxyl or alkoxycarbonyl,
(b) a 3-thiazolidyl,
(c) a piperidino substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl,
(d) a thiomorpholino,
(e) a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl,
(f) a 1-piperazyl substituted with a phenyl which may be substituted with alkylamino, halogen, alkoxy, alkyl, hydroxy, carboxyalkoxy or alkoxycarbonylalkoxy,
(g) a 1,4-diazepanyl which may be substituted with alkyl or alkylaminoalkyl, or
(h) a carboxylmorpholino.

In addition, the present invention relates to a pharmaceutical agent, such as a prophylactic agent or a therapeutic agent of a peripheral nerve disorder induced by an anticancer agent, an agent having a neurotrophic factor-like activity, or an analgesic, containing, as an active ingredient, at least one member of a trans-2-decenoic acid derivative represented by the following general formula (I) and a pharmaceutically acceptable salt thereof:

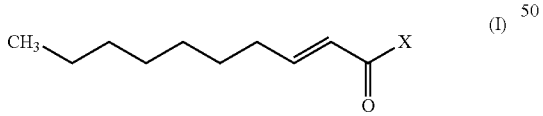

wherein X is:
(a) a 1-pyrrolidyl which may be substituted with carboxyl or alkoxycarbonyl,
(b) a 3-thiazolidyl,
(c) a piperidino which may be substituted with alkyl, oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl,
(d) a morpholino which may be substituted with carboxyl,
(e) a thiomorpholino,
(f) a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl,
(g) a 1-piperazyl substituted with a phenyl which may be substituted with alkylamino, halogen, alkoxy, alkyl, hydroxy, carboxyalkoxy or alkoxycarbonylalkoxy,
(h) a 1-azepanyl, or
(i) a 1,4-diazepanyl which may be substituted with alkyl or alkylaminoalkyl. The compound represented by the general formula (I) embraces the compound represented by the general formula (I') mentioned above.

In the substituents of the general formulae (I) and (I') mentioned above, the alkyl (including "alkyl" in alkylamino, alkylaminoalkyl, carboxyalkyl, alkoxycarbonylalkyl, piperidinoalkyl, phenylalkyl, carboxyphenylalkyl, or alkoxycarbonylphenylalkyl) may be any ones, and the alkyl is linear or branched alkyl groups having from 1 to 4 carbon atoms, preferably including methyl, ethyl, propyl, isopropyl, butyl, isobutyl, sec-butyl, t-butyl, etc. Also, the alkylamino (including "alkylamino" in alkylaminoalkyl) refers to an amino group substituted with 1 or 2 alkyls.

The alkoxy (including "alkoxy" in alkoxycarbonyl, carboxyalkoxy, or alkoxycarbonylalkoxy) may be any ones, and the alkoxy is a linear or branched alkoxy group having from 1 to 4 carbon atoms, preferably including methoxy, ethoxy, n-propoxy, isopropoxy, n-butoxy, isobutoxy, sec-butoxy, t-butoxy, etc.

The cycloalkyl may be any ones, and the cycloalkyl is a cycloalkyl group having from 3 to 8 carbon atoms, preferably including cyclopropyl, cyclobutyl, cyclopentyl, cyclohexyl, cycloheptyl, cyclooctyl, etc., and more preferably a cycloalkyl group having 5 or 6 carbon atoms.

The halogen (including "halogeno" in the halogenophenyl) is fluorine, chlorine, bromine, iodine, etc.

The compound represented by the general formula (I) (including the compound represented by the formula (I'); hereinafter referred to the same) of the present invention can be produced using trans-2-decenoic acid as a raw material in the manner, for example, as shown in the following reaction formula:

Reaction Formula

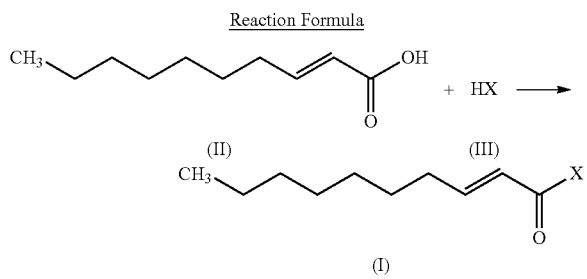

wherein X is as defined above.

The compound represented by the general formula (I) can be produced by subjecting a compound represented by the general formula (II) and a compound represented by the general formula (III) having an active hydrogen to dehydration condensation. As the dehydration condensation reaction, a known method can be employed. For example, a compound represented by the general formula (II) and a compound represented by the general formula (III) can be allowed to react in the presence of an appropriate condensing agent, including, for example, dicyclohexylcarbodiimide (DCC) or N-(3-dimethylaminopropyl)-N'-ethylcarbodiimide.HCl. The reaction may be usually carried out in a solvent, including, for example, dichloromethane. The amount of the compound represented by the general formula (III) used is usually from 0.5 to 2 mol, and preferably from 1 to 1.5 mol, per one mol of the compound represented by the general formula (II).

Alternatively, for example, the compound represented by the general formula (II) is once converted to a carboxylic halide, and thereafter allowed to react with a compound represented by the general formula (3) in the presence or absence of a base. The conversion to the carboxylic halide may be carried out, for example, using a halogenating agent such as thionyl chloride, sulfuryl chloride, phosphorus trichloride, phosphorus pentachloride, oxalyl chloride or phosphoric acid trichloride. Examples of the base include triethylamine and pyridine. The amount of the compound represented by the general formula (III) used is usually from 0.5 to 2 mol, and preferably from 1 to 1.5 mol, per one mol of the compound represented by the general formula (II). When a base is used, the amount of the base used is usually from 1 to 5 mol or so, per one mol of the compound represented by the general formula (II).

After the termination of the above reaction, known purification and isolation procedures, including, for example, extraction, chromatography, distillation, or recrystallization, are employed, whereby an intended compound can be obtained.

Examples of the compound produced as such are shown in Tables 1 to 5. When each compound is referred to hereinafter, the compound number mentioned in the tables is used.

TABLE 1

| No. | Compound Name | Structural Formula |
|---|---|---|
| 1 | 1-((E)-2-Decenoyl)pyrrolidine | |
| 2 | (S)-1-((E)-2-Decenoyl)pyrrolidine-2-carboxylic acid | |
| 3 | Methyl (S)-1-((E)-2-Decenoyl)-pyrrolidine-2-carboxylate | |
| 4 | 3-((E)-2-Decenoyl)thiazolidine | |
| 5 | 1-((E)-2-Decenoyl)piperidine | |
| 6 | 1-((E)-2-Decenoyl)-4-methylpiperidine | |
| 7 | 1-((E)-2-Decenoyl)-piperidin-4-one | |

TABLE 1-continued

| No. | Compound Name | Structural Formula |
|---|---|---|
| 8 | 1-((E)-2-Decenoyl)-4-hydroxypiperidine | |
| 9 | 1-((E)-2-Decenoyl)-4-methoxypiperidine | |
| 10 | 1-((E)-2-Decenoyl)piperidine-4-carboxylic acid | |
| 11 | Ethyl 1-((E)-2-Decenoyl)-piperidine-4-carboxylate | |
| 12 | 1-((E)-2-Decenoyl)-4-dimethylaminopiperidine | |
| 13 | 1-((E)-2-Decenoyl)-4-diethylaminopiperidine | |

TABLE 2

| No. | Compound Name | Structural Formula |
|---|---|---|
| 14 | 1-((E)-2-Decenoyl)-4-diethylaminomethylpiperidine | |
| 15 | 1-((E)-2-Decenoyl)-4-(2-dimethylaminoethyl)piperidine | |

TABLE 2-continued

| No. | Compound Name | Structural Formula |
|---|---|---|
| 16 | 1-((E)-2-Decenoyl)-4-phenylpiperidine | |
| 17 | 4-((E)-2-Decenoyl)morpholine | |
| 18 | 4-((E)-2-Decenoyl)-thiomorpholine | |
| 19 | 1-((E)-2-Decenoyl)-4-methylpiperazine | |
| 20 | 1-((E)-2-Decenoyl)-4-isopropylpiperazine | |
| 21 | 3-[4-((E)-2-Decenoyl)piperazin-1-yl]propionic acid | |
| 22 | 1-((E)-2-Decenoyl)-4-[2-(dimethylamino)ethyl]piperazine | |
| 23 | 4-Cyclohexyl-1-((E)-2-decenoyl)piperazine | |

TABLE 2-continued

| No. | Compound Name | Structural Formula |
| --- | --- | --- |
| 24 | 1-((E)-2-Decenoyl)-4-(2-piperidin-1-ylethyl)piperazine | |

TABLE 3

| No. | Compound Name | Structural Formula |
| --- | --- | --- |
| 25 | 1-((E)-2-Decenoyl)-4-phenylpiperazine | |
| 26 | 4-Benzyl-1-((E)-2-decenoyl)-piperazine | |
| 27 | 1-((E)-2-Decenoyl)-4-(2-phenylethyl)piperazine | |
| 28 | 1-((E)-2-Decenoyl)-4-(4-dimethylaminophenyl)-piperazine | |
| 29 | 1-((E)-2-Decenoyl)-4-(pyridin-4-yl)piperazine | |

TABLE 3-continued

| No. | Compound Name | Structural Formula |
|-----|---------------|--------------------|
| 30 | 1-((E)-2-Decenoyl)-4-(pyridin-2-yl)piperazine | |
| 31 | 1-((E)-2-Decenoyl)-4-(pyrimidin-2-yl)piperazine | |
| 32 | 1-((E)-2-Decenoyl)azepane | |
| 33 | 1-((E)-2-Decenoyl)-4-methyl-[1,4]diazepane | |
| 34 | 1-((E)-2-Decenoyl)-4-(2-dimethylaminoethyl)-[1,4]diazepane | |

TABLE 4

| No. | Compound Name | Structural Formula |
|-----|---------------|--------------------|
| 35 | 2-(1-((E)-2-Decenoyl)-4-piperidyl)acetic acid | |
| 36 | 3-(1-((E)-2-Decenoyl)-4-piperidyl)propanoic acid | |
| 37 | 1-((E)-2-Decenoyl)-4-cyanopiperidine | |

TABLE 4-continued

| No. | Compound Name | Structural Formula |
|---|---|---|
| 38 | 1-((E)-2-Decenoyl)-4-(4-chlorophenyl)piperidine | |
| 39 | [4-[(E)-2-Decenoyl)-piperazin-1-yl]acetic acid hydrochloride | |
| 40 | 4-[4-[(E)-2-Decenoyl)-piperazin-1-yl]butanoic acid hydrochloride | |
| 41 | 1-((E)-2-Decenoyl)-4-(4-chlorophenyl)piperazine | |
| 42 | 1-((E)-2-Decenoyl)-4-(4-methoxyphenyl)piperazine | |
| 43 | 1-((E)-2-Decenoyl)-4-(4-methylphenyl)piperazine | |
| 44 | 1-((E)-2-Decenoyl)-4-(4-fluorophenyl)piperazine | |

TABLE 5

| No. | Compound Name | Structural Formula |
|---|---|---|
| 45 | 1-((E)-2-Decenoyl)-4-(2-chlorophenyl)piperazine | |
| 46 | 1-((E)-2-Decenoyl)-4-(4-hydroxyphenyl)piperazine | |
| 47 | 2-[4-[4-((E)-2-Decenoyl)piperazin-1-yl]-phenoxy]acetic acid | |
| 48 | 4-[[4-((E)-2-Decenoyl)piperazin-1-yl]methyl]benzoic acid | |
| 49 | 4-[(E)-2-Decenoyl]morpholin-3-carboxylic acid | |

The compound represented by the general formula (I) of the present invention includes not only the free forms mentioned above, but also those in the forms of salts, solvates, and prodrug. When a salt is formed, in a case where a compound is used as a pharmaceutical agent, the form of a pharmaceutically acceptable salt is preferred. Examples of the salts include addition salts with an acid such as phosphoric acid, hydrochloric acid, sulfuric acid, nitric acid, hydrobromic acid, perchloric acid, thiocyanic acid, boric acid, formic acid, acetic acid, haloacetic acid, propionic acid, citric acid, tartaric acid, lactic acid, glycolic acid, succinic acid, gluconic acid, malonic acid, fumaric acid, anthranilic acid, benzoic acid, cinnamic acid, p-toluenesulfonic acid, naphthalenesulfonic acid, or sulfanilic acid. Also, the salts include salts with a metal, such as an alkali metal such as sodium or potassium, an alkaline earth metal such as calcium or magnesium, or aluminum; and salts with a base such as ammonia or an organic amine. These salts can be produced from each compound in a free form, or converted reversibly, in accordance with a known method. The solvates include hydrates, alcoholates, etc. In addition, in a case where the compound represented by the general formula (I) of the present invention contains an asymmetric carbon, the compound also embraces various isomers such as optical isomers, racemic mixtures, and diastereomers. In a case where the compound of the present invention is formed into crystals, the crystals also embrace various kinds of crystalline forms (crystal polymorphisms) which can be formed thereby.

The compound represented by the general formula (I) of the present invention is effective as an agent for having prophylactic or therapeutic action for a peripheral nerve disorder induced by administration of anti-cancer agents. One of the anti-cancer agents developing the peripheral nerve disorder is an anti-cancer agent that damages microtubules to induce the peripheral nerve disorder. Examples of such medicinal agent include taxane drug such as paclitaxel or docetaxel, and vinca alkaloid drug such as vincristine, vinplastine, vindesine or vinorelbine. Another anti-cancer agent is an anti-cancer agent that damages nerve cells to cause axonopathy and then induces the peripheral nerve disorder. Examples of such agents include platinum formulation such as oxaliplatin, carboplatin, cisplatin or nedaplatin.

Examples of the peripheral nerve disorder induced by these anti-cancer agents include pains such as a stinging pain and burning pain, numbness of limb extremities, paresthesia such as a burning sensation, hyperesthesia such as hypersensitivity to cold stimuli, dysesthesia such as sensory loss, sensory paralysis and sense of discomfort, sensory ataxia and muscle weakness. The peripheral nerve disorder induced by anti-cancer agents targeted for the prevention or treatment in the compounds of the present invention includes a peripheral nerve disorder induced by monotherapy using one of anti-cancer agents as well as a peripheral nerve disorder induced by multiple drug therapy in which a plurality of medicinal agents having various action mechanisms are together administered or by biochemical modulation in which a combination of medicinal agents and an administration method are designed such that the medicinal agents having various action mechanisms can provide the maximum effectiveness.

Since the compound represented by the general formula (I) of the present invention has a neurotrophic factor-like activity, the compound is useful as an agent having a neurotrophic factor-like activity, and is useful in the prevention and treatment of nervous disorders. The nervous disorder refers to a clinical condition of damaging functions of nerve cells due to degeneration or cell death of the nerve cells, and includes neurodegenerative diseases and mental diseases. The neurodegenerative diseases refer to dementia, Alzheimer's disease, Parkinson's disease, amyotrophic lateral sclerosis (ALS), Huntington's disease, progressive supranuclear palsy (PSP), diabetic neuropathy, glaucoma of optic nerve diseases etc. The mental diseases refer to depression (including bipolar depression), anxiety disorder (neurosis), integration disorder syndrome, autistic disorder spectrum etc. When the agent is used for depression, it takes at least 3 to 4 weeks until there appear effects of conventionally existing depression therapeutic agents such as a tricyclic antidepressant, a tetracyclic antidepressant, a selective serotonin reuptake inhibitor (SSRI), a serotonin noradrenalin reuptake inhibitor (SNRI), and the like, and these agents had to be taken periodically during this term; however, the pharmaceutical agent containing the compound of the present invention can be expected to have immediate affectivity as compared to existing medical drugs.

The compound represented by the general formula (I) is useful as a therapeutic agent (repairing agent) for spinal cord injury. There are no effective methods of treatment for spinal cord injury suffering physical damages caused by traffic accidents, athletic sports accidents, or compressive fractures of elder people, and various studies on methods of treatment by regeneration therapy have been made. It is expected that the pharmaceutical agent containing the compound of the present invention can treat (repair) spinal cord injury with administrations by injections, internal medication, and external applications.

In addition, the compound represented by the general formula (I) of the present invention is useful as prophylactic agents or therapeutic agents for various pain diseases. Examples of the pain diseases include arthralgia such as the pains by osteoarthritis (e.g., knee osteoarthritis and hip osteoarthritis) or the pains by rheumatoid arthritis.

The compounds of the present invention can be made into a pharmaceutical preparation in various dosage forms (such as oral, injectable and external preparations) by appropriately combining with an appropriate pharmaceutical carrier or diluent. The pharmaceutical agent of the present invention may be a formulation in which the compound of the present invention is used together with other pharmaceutically active ingredient(s). Further, the pharmaceutical agent of the present invention may be formed into a preparation as an inclusion complex with cyclodextrin etc. As a result, there may be the cases where enhancement of pharmacological activity, improvement in stability, prolonged action, easy handling, etc. can be obtained. The inclusion complex can be formed by, for example, mixing the compound of the present invention with α-, β-, or γ-cyclodextrin in accordance with an ordinary method.

When the compound of the present invention is made into an oral preparation, a tablet, powder, granule or capsule preparation can be made by formulation of proper combinations of appropriate additives, including, for example, an excipient, a binder, a disintegrator, a lubricant, an extender, a wetting agent, a buffer, a preservative and a flavoring. When made into an injectable preparation, it is possible to make into an injectable preparation by addition of a stabilizer, a preservative, an isotonic agent or the like to a solution or suspension containing the ester of C10 fatty acid. When made into an external preparation, it is possible to make into an external preparation such as patch preparation, gel preparation, ointment, cream preparation or the like. Thus, the compound of the present invention is, for example, mixed with, melted in or emulsified in an appropriate base to make a preparation, and in the case of a patch preparation, the above is spread and applied onto a support. In the case of a patch preparation, a gel preparation or the like, it can be made, for example, into a composition using an organogelling agent. Incidentally, depending upon the dosage form of each external preparation, a commonly used preservative, antioxidant, flavoring agent, adhesive or the like may be appropriately selected and added to a formulation.

A desired dose of the compound of the present invention may be appropriately increased or decreased by taking dose regimen, age, sex, symptom in a patient, etc. into consideration, and the compound can be usually administered in an amount of from 1 to 1,000 mg, and preferably 5 to 300 mg, for adult, at once or in several divided administrations per day.

EXAMPLES

The present invention will be hereinafter explained by means of Examples, without intending to limit the present invention to these Examples.

Example 1

Production of 1-((E)-2-Decenoyl)pyrrolidine) [Compound 1]

A tetrahydrofuran solution (20 mL) of pyrrolidine (0.71 g, 0.01 mol) containing pyridine (0.79 g, 0.01 mol) was added to a tetrahydrofuran solution (20 mL) of (E)-2-decenoic acid chloride (1.9 g, 0.01 mol), synthesized using (E)-2-decenoic acid and thionyl chloride, and the mixture was heated under refluxing in a warm water bath for 3 hours. After distilling off excess tetrahydrofuran, water was added to a liquid reaction mixture, and the liquid mixture was extracted with ethyl acetate, and washed with water, and ethyl acetate was distilled off. The residue was purified with silica gel column chromatography (developing solvent:hexane:ethyl acetate=1:3), to give an intended compound (1.4 g) in the form of a colorless oily substance.

Colorless oily substance, $C_{14}H_{25}NO$ MW 223, ESIMS (positive ion mode: rel. int): m/z 246.184 [M+Na]$^+$ (Calcd for $C_{14}H_{25}NONa$, 246.1834), $^1$H-NMR (400 MHz, CDCl$_3$) δ: 0.88 (3H, t, J=6.8 Hz), 1.25_1.32 (8H, m), 1.45 (2H, m), 1.86 (2H, m), 1.96 (2H, m), 2.20 (2H, m), 3.518 (2H, t, J=7.2 Hz), 3.524 (2H, t, J=7.2 Hz), 6.09 (1H, d, J=15.4 Hz), 6.91 (1H, dt, J=15.4, 6.8 Hz).

Example 2

Production of (S)-1-((E)-2-Decenoyl)pyrrolidine-2-carboxylic acid methyl ester [Compound 3]

Triethylamine (0.84 mL, 6 mmol) and l-ethyl-3-(3-dimethylaminopropyl) carbodiimide hydrochloride (WSC.HCl) (1.05 g, 5.5 mmol) were added to a dichloromethane solution (50 mL) containing (E)-2-decenoic acid (0.92 mL, 5 mmol) and L-proline methyl ester hydrochloride (0.91 g, 5.5 mmol) at room temperature, and the mixture was stirred for 24 hours. The obtained reaction solution was washed with water and saturated sodium chloride solution, and then dried over anhydrous sodium sulfate. The residue was purified with silica gel column chromatography (hexane:ethyl acetate=7:3), to give an intended compound (1.23 g, 87%) in the form of a colorless oily substance. Here, in a case where the starting raw material amine is not a hydrochloride, triethylamine may not be added.

Colorless oily substance, $C_{16}H_{27}NO_3$ MW 281.4, EIMS: m/z 282 [M+H]$^+$, $^1$H-NMR (500 MHz, DMSO-d$_6$) δ: 0.86 (t, J=7.0 Hz, 3H), 1.21-1.31 (m, 8H), 1.34-1.44 (m, 2H), 1.70-1.97 (m, 3H), 2.02-2.27 (m, 3H), 3.38-3.65 (m, 5H), 4.31-4.35 and 4.70-4.74 (m, 1H), 5.97 and 6.25 (m, 1H), 6.61-6.71 (m, 1H).

Example 3

Production of (S)-1-((E)-2-Decenoyl)pyrrolidine-2-carboxylic acid [Compound 2]

Compound 3 (0.84 g, 3 mmol) was dissolved in methanol (40 mL), and a 1 mol/L aqueous sodium hydroxide solution (4 mL, NaOH 4 mmol) was added thereto at room temperature, and the mixture was stirred for 20 hours. The solvent was distilled off under a reduced pressure, and the residue was then dissolved in water, and a 10% aqueous citric acid solution was added thereto to adjust its pH to about 4. The liquid mixture was extracted with dichloromethane, an organic layer was washed with water and saturated sodium chloride solution, and the washed extract was then dried over anhydrous sodium sulfate, to give an intended compound (0.72 g, 90%) in the form of a colorless oily substance.

Colorless oily substance, $C_{15}H_{25}NO_3$ MW 267.4, EIMS: m/z 268 [M+H]$^+$, $^1$H-NMR (500 MHz, DMSO-d$_6$) δ: 0.86 (t, J=7.0 Hz, 3H), 1.20-1.45 (m, 10H), 1.70-2.27 (m, 6H), 3.37-3.63 (m, 2H), 4.23-4.28 and 4.55-4.59 (m, 1H), 6.25 and 5.99 (m, 1H), 6.62-6.71 (m, 1H), 12.30-12.70 (br, 1H).

Example 4

Production of 3-((E)-2-Decenoyl)thiazolidine [Compound 4]

The same procedures as in Example 1 were carried out using (E)-2-decenoic acid and thiazolidine as starting raw materials, to produce an intended compound.

Colorless oily substance, $C_{13}H_{23}NOS$ MW 241, HR-ESIMS (positive ion mode): m/z 264.1443 [M+Na]$^+$ (Calcd for $C_{13}H_{23}NOSNa$, 264.1398), $^1$H-NMR (400 MHz, CDCl$_3$) δ: 0.88 (3H, t, J=6.8 Hz), 1.22-1.34 (8H, m), 1.46 (2H, m), 2.22 (2H, m), 3.01 (1H, t, J=6.1 Hz), 3.11 (1H, t, J=6.1 Hz), 3.83 (1H, t, J=6.1 Hz), 3.91 (1H, brt), 4.58 (1H, s), 4.65 (1H, s), 6.11 (1H, d, J=15.0 Hz), 6.96 (1H, dt, J=15.0, 7.3 Hz).

Example 5

Production of 1-((E)-2-Decenoyl)piperidine [Compound 5]

The same procedures as in Example 1 were carried out using (E)-2-decenoic acid and piperidine as starting raw materials, to produce an intended compound.

Colorless oily substance, $C_{15}H_{27}NO$ MW 237, EIMS: m/z 237 [M]$^+$, $^1$H-NMR (500 MHz, CDCl$_3$) δ: 0.88 (3H, t, J=7.0 Hz), 1.22-1.34 (8H, m), 1.42-1.47 (2H, m), 1.54-1.59 (4H, m), 1.62-1.68 (2H, m), 2.16-2.21 (2H, m), 3.44-3.65 (4H, m), 6.22-6.26 (1H, m), 6.83 (1H, dt, J=15.1, 7.1 Hz)

Example 6

Production of 1-((E)-2-Decenoyl)-4-methylpiperidine [Compound 6]

The same procedures as in Example 2 were carried out using (E)-2-decenoic acid and 4-methylpiperidine as starting raw materials, to produce an intended compound.

Colorless oily substance, $C_{16}H_{29}NO$ MW 251.4, EIMS: m/z 252 [M+H]$^+$, $^1$H-NMR (500 MHz, DMSO-d$_6$) δ: 0.93-1.11 (m, 8H), 1.20-1.32 (m, 8H), 1.35-1.44 (m, 2H), 1.54-1.67 (m, 3H), 2.12-2.19 (m, 2H), 2.51-2.60 (m, 1H), 2.92-3.11 (m, 1H), 3.96-4.15 (m, 1H), 4.32-4.41 (m, 1H), 6.43 (d, J=15.0 Hz, 1H), 6.61 (dt, J=15.0, 7.0 Hz, 1H).

Example 7

Production of 1-((E)-2-decenoyl)piperidin-4-one [Compound 7]

The same procedures as in Example 1 were carried out using (E)-2-decenoic acid and piperidin-4-one as starting raw materials, to produce an intended compound.

Pale yellow oily substance, $C_{15}H_{25}NO_2$ MW 251, HR-ESIMS (positive ion mode): m/z 274.1824 [M+Na]$^+$ (Calcd for $C_{15}H_{25}NO_2Na$, 274.1783), $^1$H-NMR (400 MHz, CDCl$_3$) δ: 0.88 (3H, t, J=6.8 Hz), 1.22-1.35 (8H, m), 1.47 (2H, m), 2.23 (2H, m), 2.51 (4H, t, J=6.4 Hz) 3.82-3.97 (4H, m), 6.31 (1H, d, J=15.2 Hz), 6.97 (1H, dt, J=15.2, 7.3 Hz).

Example 8

Production of 1-((E)-2-Decenoyl)-4-hydroxypiperidine [Compound 8]

The same procedures as in Example 2 were carried out using (E)-2-decenoic acid and 4-hydroxypiperidine as starting raw materials, to produce an intended compound.

Colorless oily substance, $C_{15}H_{27}NO_2$ MW 253.4, EIMS: m/z 254 [M+H]$^+$, $^1$H-NMR (500 MHz, DMSO-d$_6$) δ: 0.86 (t, J=7.0 Hz, 3H), 1.20-1.32 (m, 10H), 1.36-1.44 (m, 2H), 1.66-1.76 (m, 2H), 2.13-2.20 (m, 2H), 3.00-3.09 (m, 1H), 3.16-3.25 (m, 1H), 3.65-3.73 (m, 1H), 3.76-3.84 (m, 1H), 3.88-3.96 (m, 1H), 4.74 (d, J=4.1 Hz, 1H), 6.45 (d, J=15.0 Hz, 1H), 6.63 (dt, J=15.0, 7.0 Hz, 1H).

Example 9

Production of 1-((E)-2-Decenoyl)-4-methoxypiperidine [Compound 9]

Compound 8 (0.62 g, 2.4 mmol) was dissolved in THF (10 mL), and sodium hydride (60% in mineral oil) (0.10 g, 2.6 mmol) was added thereto under ice-cooling. After mixing for 15 minutes under ice-cooling, methyl iodide (0.16 mL, 2.6 mmol) was added thereto, and stirred at room temperature for 20 hours. Water was added to the liquid reaction mixture, the mixture was extracted with ethyl acetate, an organic layer was washed with water and saturated sodium chloride solution, and the washed extract was then dried over anhydrous sodium sulfate. The residue was purified with silica gel column chromatography (developing solvent: hexane:ethyl acetate=3:2), to give an intended compound (0.42 g, 65%) in the form of a pale yellow oily substance.

Pale yellow oily substance, $C_{16}H_{29}NO_2$ MW 267.4, EIMS:

m/z 268 [M+H]$^+$, $^1$H-NMR (500 MHz, DMSO-d$_6$) δ: 0.86 (t, J=7.0 Hz, 3H), 1.20-1.43 (m, 12H), 1.75-1.85 (m, 2H), 2.12-2.19 (m, 2H), 3.08-3.17 (m, 1H), 3.22-3.30 (m, 1H), 3.25 (s, 3H), 3.33-3.42 (m, 1H), 3.70-3.88 (m, 2H), 6.45 (d, J=15.0 Hz, 1H), 6.63 (dt, J=15.0, 7.0 Hz, 1H).

Example 10

Production of 1-((E)-2-Decenoyl)piperidine-4-carboxylic acid [Compound 10]

The same procedures as in Example 3 were carried out using Compound 11 as a starting raw material, to produce an intended compound. White crystals, mp 88°-89° C., $C_{16}H_{27}NO_3$ MW 281.4, EIMS: m/z 281 [M]$^+$, $^1$H-NMR (500 MHz, DMSO-d$_6$) δ: 0.86 (t, J=7.0 Hz, 3H), 1.19-1.31 (m, 8H), 1.32-1.46 (m, 4H), 1.77-1.87 (m, 2H), 2.12-2.20 (m, 2H), 2.46-2.54 (m, 1H), 2.71-2.82 (m, 1H), 3.03-3.16 (m, 1H), 3.90-4.00 (m, 1H), 4.18-4.28 (m, 1H), 6.44 (d, J=15.0 Hz, 1H), 6.63 (dt, J=15.0, 7.0 Hz, 1H), 12.28 (brs, 1H).

Example 11

Production of 1-((E)-2-Decenoyl)piperidine-4-carboxylic acid ethyl ester [Compound 11]

The same procedures as in Example 2 were carried out using (E)-2-decenoic acid and ethyl isonipecotate as starting raw materials, to produce an intended compound.

Colorless oily substance, $C_{18}H_{31}NO_3$ MW 309.4, EIMS: m/z 309 [M]$^+$, $^1$H-NMR (500 MHz, DMSO-d$_6$) δ: 0.86 (t, J=7.0 Hz, 3H), 1.18 (t, J=7.0 Hz, 3H), 1.20-1.32 (m, 8H), 1.33-1.49 (m, 4H), 1.80-1.88 (m, 2H), 2.13-2.19 (m, 2H), 2.56-2.64 (m, 1H), 2.71-2.81 (m, 1H), 3.05-3.16 (m, 1H), 3.92-4.07 (m, 1H), 4.07 (q, J=7.0 Hz, 2H), 4.20-4.28 (m, 1H), 6.45 (d, J=15.0 Hz, 1H), 6.63 (dt, J=15.0, 7.0 Hz, 1H).

Example 12

Production of 1-((E)-2-decenoyl)-4-dimethylaminopiperidine [Compound 12]

The same procedures as in Example 2 were carried out using (E)-2-decenoic acid and 4-dimethylaminopiperidine as starting raw materials, to produce an intended compound.

Pale yellow oily substance, $C_1H_{32}N_2O$ MW 280.5, EIMS:

m/z 281 [M+H]$^+$, $^1$H-NMR (500 MHz, DMSO-d$_6$) δ: 0.86 (t, J=7.0 Hz, 3H), 1.13-1.31 (m, 10H), 1.36-1.44 (m, 2H), 1.70-1.79 (m, 2H), 2.12-2.20 (m, 7H), 2.26-2.34 (m, 1H), 2.56-2.65 (m, 1H), 2.93-3.04 (m, 1H), 3.99-4.07 (m, 1H), 4.33-4.41 (m, 1H), 6.45 (d, J=15.0 Hz, 1H), 6.63 (dt, J=15.0, 7.0 Hz, 1H).

In addition, an oily product Compound 12 was dissolved in methylene chloride, and treated with hydrogen chloride-dioxane, to produce 1-((E)-2-decenoyl)-4-dimethylaminopiperidine hydrochloride (crystals, mp 185°-188° C.).

Example 13

Production of 1-((E)-2-Decenoyl)-4-diethylaminopiperidine [Compound 13]

The same procedures as in Example 2 were carried out using (E)-2-decenoic acid and 4-diethylaminopiperidine as starting raw materials, to produce an intended compound.

Pale yellow oily substance, $C_{19}H_{36}N_2O$ MW 308.5, EIMS:

m/z 309 [M+H]$^+$, $^1$H-NMR (500 MHz, DMSO-d$_6$) δ: 0.86 (t, J=7.0 Hz, 3H), 0.95 (t, J=7.0 Hz, 6H), 1.15-1.31 (m, 10H), 1.36-1.43 (m, 2H), 1.63-1.72 (m, 2H), 2.13-2.20 (m, 2H), 2.45 (q, J=7.0 Hz, 4H), 2.50-2.60 (m, 1H), 2.65-2.73 (m, 1H), 2.90-3.02 (m, 1H), 4.01-4.10 (m, 1H), 4.39-4.47 (m, 1H), 6.44 (d, J=15.0 Hz, 1H), 6.61 (dt, J=15.0, 7.0 Hz, 1H).

Example 14

Production of 1-((E)-2-Decenoyl)-4-diethylaminomethylpiperidine [Compound 14]

The same procedures as in Example 2 were carried out using (E)-2-decenoic acid and 4-(diethylaminomethyl)piperidine as starting raw materials, to produce an intended compound.

Pale red oily substance, $C_{20}H_{38}N_2O$ MW 322.5, EIMS: m/z 323 [M+H]$^+$, $^1$H-NMR (500 MHz, DMSO-d$_6$) δ: 0.86 (t, J=7.0 Hz, 3H), 0.93 (t, J=7.0 Hz, 6H), 0.90-0.97 (m, 2H), 1.20-1.30 (m, 8H), 1.35-1.43 (m, 2H), 1.60-1.80 (m, 3H), 2.10-2.19 (m, 4H), 2.41 (q, J=7.0 Hz, 4H), 2.51-2.60 (m, 1H), 2.92-3.02

(m, 1H), 3.97-4.06 (m, 1H), 4.33-4.42 (m, 1H), 6.43 (d, J=15.0 Hz, 1H), 6.61 (dt, J=15.0, 7.0 Hz, 1H).

Example 15

Production of 1-((E)-2-Decenoyl-4-(2-dimethylaminoethyl)piperidine [Compound 15]

The same procedures as in Example 2 were carried out using (E)-2-decenoic acid and 4-(2-dimethylaminoethyl) piperidine as starting raw materials, to produce an intended compound.
Pale yellow oily substance, $C_{19}H_{36}N_2O$ MW 308.5, EIMS: m/z 309 [M+H]$^+$, $^1$H-NMR (500 MHz, DMSO-d$_6$) δ: 0.86 (t, J=7.0 Hz, 3H), 0.90-1.15 (m, 2H), 1.20-1.34 (m, 10H), 1.35-1.43 (m, 2H), 1.48-1.59 (m, 1H), 1.62-1.71 (m, 2H), 2.09 (s, 6H), 2.13-2.22 (m, 4H), 2.50-2.58 (m, 1H), 2.90-3.01 (m, 1H), 3.95-4.05 (m, 1H), 4.32-4.41 (m, 1H), 6.43 (d, J =15.0 Hz, 1H), 6.60 (dt, J=15.0, 7.0 Hz, 1H).

Example 16

Production of 1-((E)-2-Decenoyl)-4-phenyl piperidine [Compound 16]

The same procedures as in Example 1 were carried out using (E)-2-decenoic acid and 4-phenylpiperidine as starting raw materials, to produce an intended compound.
Colorless oily substance, $C_{21}H_{31}NO$ MW 313, HR-ES-IMS (positive ion mode): m/z 336.2330 [M+Na]$^+$ (Calcd for $C_{21}H_{31}NONa$, 336.2303),
$^1$H-NMR (400 MHz, CDCl$_3$) δ: 0.88 (3H, t, J=7.2 Hz), 1.22-1.34 (8H, m), 1.46 (2H, m), 1.66 (2H, m), 1.91 (2H, brd), 2.21 (2H, m), 2.66-2.80 (2H, m), 3.15 (1H, brt), 4.14 (1H, brd), 4.84 (1H, brd), 6.29 (1H, d, J=15.0 Hz), 6.89 (1H, dt, J=15.0, 7.3 Hz), 7.18-7.24 (3H, m), 7.32 (2H, t, J=7.4 Hz).

Example 17

Production of 4-((E)-2-Decenoyl)morpholine [Compound 17]

The same procedures as in Example 1 were carried out using (E)-2-decenoic acid and morpholine as starting raw materials, to produce an intended compound.
Colorless oily substance, $C_{14}H_{25}NO_2$ MW 239, HR-ES-IMS (positive ion mode): m/z 262.1827 [M+Na]$^+$ (Calcd for $C_{14}H_{25}NO_2Na$, 262.1783),
$^1$H-NMR (400 MHz, CDCl$_3$) δ: 0.88 (3H, t, J=7.2 Hz), 1.24-1.33 (8H, m), 1.45 (2H, m), 2.20 (2H, m), 3.57 (2H, brs), 3.69 (6H, brs), 6.20 (1H, d, J=15.2 Hz), 6.91 (1H, dt, J=15.2, 7.1 Hz).

Example 18

Production of 4-((E)-2-decenoyl)thiomorpholine [Compound 18]

The same procedures as in Example 1 were carried out using (E)-2-decenoic acid and thiomorpholine as starting raw materials, to produce an intended compound.
Colorless oily substance, $C_{14}H_{25}NOS$ MW 255, HR-ESIMS (positive ion mode): m/z 278.1575 [M+Na]$^+$ (Calcd for $C_{14}H_{25}NOSNa$, 278.1555),
$^1$H-NMR (400 MHz, CDCl$_3$) δ: 0.88 (3H, t, J=7.2 Hz), 1.23-1.33 (8H, m), 1.45 (2H, m), 2.20 (2H, m), 2.63 (4H, brs), 3.83 (2H, brs), 3.92 (2H, brs), 6.20 (1H, d, J=15.2 Hz), 6.87 (1H, dt, J=15.2, 7.3 Hz).

Example 19

Production of 1-((E)-2-Decenoyl)-4-methylpiperazine [Compound 19]

The same procedures as in Example 2 were carried out using (E)-2-decenoic acid and 1-methylpiperazine as starting raw materials, to produce an intended compound.
Pale yellow oily substance, $C_{15}H_{28}N_2O$ MW 252.4, EIMS:
m/z 253 [M+H]$^+$, $^1$H-NMR (500 MHz, DMSO-d$_6$) δ: 0.86 (t, J=7.0 Hz, 3H), 1.20-1.31 (m, 8H), 1.35-1.44 (m, 2H), 2.13-2.19 (m, 2H), 2.17 (s, 3H), 2.22-2.30 (m, 4H), 3.45-3.55 (m, 4H), 6.44 (dt, Jd=14.0 Hz, Jt=1.1 Hz, 1H), 6.65 (dt, J=14.0, 7.2 Hz, 1H).

Example 20

Production of 1-((E)-2-Decenoyl)-4-isopropylpiperazine [Compound 20]

The same procedures as in Example 2 were carried out using (E)-2-decenoic acid and 1-isopropylpiperazine as starting raw materials, to produce an intended compound.
Pale yellow oily substance, $C_{17}H_{32}N_2O$ MW 280.5, EIMS: m/z 280 [M]$^+$,
$^1$H-NMR (500 MHz, DMSO-d$_6$) δ: 0.86 (t, J=7.0 Hz, 3H), 0.96 (d, J=6.5 Hz, 6H), 1.20-1.31 (m, 8H), 1.36-1.42 (m, 2H), 2.11-2.20 (m, 2H), 2.35-2.42 (m, 4H), 2.65 (qq, J=6.5, 6.5 Hz, 1H), 3.44-3.54 (m, 4H), 6.43 (dt, J=15.0, 1.1 Hz, 1H), 6.63 (dt, J=15.0, 7.0 Hz, 1H).

Example 21

Production of 3-[4-((E)-2-decenoyl)piperazin-1-yl]propionic acid [Compound 21]

The same procedures as in Example 2 were carried out using (E)-2-decenoic acid and ethyl 3-piperazin-1-yl propionate dihydrochloride (ethyl ester of Compound 21) as starting raw materials, to produce ethyl 3-[4-((E)-2-decenoyl)piperazin-1-yl]propionate, and subjected to alkali saponification, to obtain an intended compound as white crystals. White crystals, mp 53°-55° C., $C_{17}H_{30}N_2O_3$ MW 310.4, EIMS: m/z 311 [M+H]$^+$, $^1$H-NMR (500 MHz, DMSO-d$_6$) δ: 0.86 (t, J=7.0 Hz, 3H), 1.19-1.31 (m, 8H), 1.35-1.44 (m, 2H), 2.12-2.20 (m, 2H), 2.32-2.43 (m, 6H), 2.55-2.61 (m, 2H), 3.43-3.57 (m, 4H), 6.45 (d, J=15.0 Hz, 1H), 6.65 (dt, J=15.0, 7.0 Hz, 1H), 11.70-12.70 (brs, 1H).
In addition, the low-melting point crystals Compound 21 were dissolved in methylene chloride, and treated with hydrogen chloride-dioxane, to produce 3-[4((E)-2-decenoyl) piperazin-1-yl]propionic acid hydrochloride (crystals, mp 201°-203° C.).

Example 22

Production of 1-((E)-2-Decenoyl)-4-[2-(dimethylamino)ethyl]piperazine [Compound 22]

The same procedures as in Example 1 were carried out using (E)-2-decenoic acid and 1-[2-(dimethylamino)ethyl] piperazine as starting raw materials, to produce an intended compound.

Oily substance, $C_{18}H_{35}N_3O$ MW 309, HR-ESIMS (positive ion mode):

m/z 310.2868 [M+H]$^+$ (calcd for $C_{18}H_{36}N_3O$, 310.2858),
$^1$H-NMR (500 MHz, CDCl$_3$) δ: 0.88 (3H, t, J=7.4 Hz), 1.27_1.31 (8H, m), 1.45 (2H, br t, J=7.5 Hz), 2.19 (2H, dt, J=6.9, 8.0 Hz), 2.32 (6H, s), 2.47 (4H, br s), 2.53 (4H, s), 3.56 (2H, br s), 3.68 (2H, br s), 6.21 (1H, d, J=15.2 Hz), 6.86 (1H, dt, J=6.9, 15.2 Hz).

Example 23

Production of 4-Cyclohexyl-1-((E)-2-decenoyl)piperazine [Compound 23]

The same procedures as in Example 2 were carried out using (E)-2-decenoic acid and 1-cyclohexylpiperazine as starting raw materials, to produce an intended compound.

White crystals, mp 33°-34° C., $C_{20}H_{36}N_2O$ MW 320.5, EIMS: m/z 320 [M]$^+$,
$^1$H-NMR (500 MHz, DMSO-d$_6$) δ: 0.85 (t, J=7.0 Hz, 3H), 1.01-1.11 (m, 1H), 1.11-1.21 (m, 4H), 1.21-1.31 (m, 8H), 1.36-1.43 (m, 2H), 1.53-1.59 (m, 1H), 1.68-1.76 (m, 4H), 2.13-2.28 (m, 3H), 2.40-2.48 (m, 4H), 3.41-3.53 (m, 4H), 6.43 (d, J=15.0 Hz, 1H), 6.64 (dt, J=15.0, 7.0 Hz, 1H).

Example 24

Production of 1-((E)-2-Decenoyl)-4-(2-piperidin-1-ylethyl)piperazine [Compound 24]

The same procedures as in Example 2 were carried out using (E)-2-decenoic acid and 1-[2-(1-piperidinyl)ethyl]piperazine as starting raw materials, to produce an intended compound.

White crystals, $C_{21}H_{39}N_3O$ MW 349.6, EIMS: m/z 350 [M+H]$^+$, $^1$H-NMR (500 MHz, DMSO-d$_6$) δ: 0.86 (t, J=6.7 Hz, 3H), 1.20-1.31 (m, 8H), 1.32-1.42 (m, 4H), 1.43-1.50 (m, 4H), 2.11-2.20 (m, 2H), 2.27-2.43 (m, 12H), 3.42-3.53 (m, 4H), 6.43 (d, J=15.0 Hz, 1H), 6.64 (dt, J=15.0, 7.0 Hz, 1H).

Example 25

Production of 1-((E)-2-Decenoyl)-4-phenylpiperazine [Compound 25]

The same procedures as in Example 1 were carried out using (E)-2-decenoic acid and 1-phenylpiperazine as starting raw materials, to produce an intended compound.

Pink oily substance, $C_{20}H_{30}N_2O$ MW 314, HR-ESIMS (positive ion mode): m/z 337.2244 [M+Na]$^+$ (Calcd for $C_{20}H_{30}N_2ONa$, 337.2256),
$^1$H-NMR (400 MHz, CDCl$_3$) δ: 0.88 (3H, t, J=6.8 Hz), 1.21-1.36 (8H, m), 1.46 (2H, m), 2.22 (2H, m), 3.18 (4H, t, J=5.4 Hz), 3.71 (2H, brs), 3.83 (2H, brs), 6.27 (1H, d, J=15.6 Hz), 6.88-6.96 (4H, m), 7.26-7.30 (2H, m).

Example 26

Production of 4-Benzyl-1-((E)-2-decenoyl)piperazine [Compound 26]

The same procedures as in Example 2 were carried out using (E)-2-decenoic acid and 1-benzylpiperazine dihydrochloride as starting raw materials, to produce an intended compound.

White crystals, mp 62°-63° C., $C_{21}H_{32}N_2O$ MW 328.5, EIMS:

m/z 2329 [M+H]$^+$, $^1$H-NMR (500 MHz, DMSO-d$_6$) δ: 0.86 (t, J=7.0 Hz, 3H), 1.19-1.31 (m, 8H), 1.35-1.42 (m, 2H), 2.11-2.19 (m, 2H), 2.28-2.38 (m, 4H), 3.48 (s, 2H), 3.48-3.57 (m, 4H), 6.43 (d, J=15.0 Hz, 1H), 6.65 (dt, J=15.0, 7.0 Hz, 1H), 7.22-7.36 (m, 5H).

Example 27

Production of 1-((E)-2-Decenoyl)-4-(2-phenylethyl)piperazine [Compound 27]

The same procedures as in Example 2 were carried out using (E)-2-decenoic acid and 1-(2-phenetyl)piperazine dihydrochloride as starting raw materials, to produce an intended compound.

White crystals, mp 33°-34° C., $C_{22}H_{34}N_2O$ MW 342.5, EIMS:

m/z 343 [M+H]$^+$, $^1$H-NMR (500 MHz, DMSO-d$_6$) δ: 0.86 (t, J=7.0 Hz, 3H), 1.19-1.31 (m, 8H), 1.36-1.44 (m, 2H), 2.11-2.21 (m, 2H), 2.36-2.45 (m, 4H), 2.52 (dd, J=6.5, 8.3 Hz, 2H), 2.74 (dd, J=6.5, 8.3 Hz, 2H), 3.46-3.56 (m, 4H), 6.45 (d, J=15.0 Hz, 1H), 6.66 (dt, J=15.0, 7.0 Hz, 1H), 7.15-7.31 (m, 5H).

Example 28

Production of 1-((E)-2-Decenoyl)-4-(4-dimethylaminophenyl)piperazine [Compound 28]

The same procedures as in Example 2 were carried out using (E)-2-decenoic acid and 1-(4-dimethylaminophenyl)piperazine dihydrochloride as starting raw materials, to produce an intended compound.

Pale brown crystals, mp 73°-74° C., $C_{22}H_{35}N_3O$ MW 357.5, EIMS: m/z 357 [M]$^+$, $^1$H-NMR (500 MHz, DMSO-d$_6$) δ: 0.85 (t, J=7.0 Hz, 3H), 1.20-1.31 (m, 8H), 1.36-1.46 (m, 2H), 2.15-2.21 (m, 2H), 2.78 (s, 6H), 2.87-2.96 (m, 4H), 3.55-3.74 (m, 4H), 6.49 (d, J=15.0 Hz, 1H), 6.64-6.72 (m, 3H), 6.86 (d, J=8.7 Hz, 2H).

Example 29

Production of 1-((E)-2-Decenoyl)-4-(pyridin-4-yl)piperazine [Compound 29]

The same procedures as in Example 1 were carried out using (E)-2-decenoic acid and 1-(4-pyridyl)piperazine as starting raw materials, to produce an intended compound.

Pale brown oily substance, $C_{19}H_{29}N_3O$ MW 315, HR-ESIMS (positive ion mode): m/z 316.2349 [M+H]$^+$ (Calcd for $C_{19}H_{30}N_3O$, 316.2383),
$^1$H-NMR (400 MHz, CDCl$_3$) δ: 0.89 (3H, t, J=7.2 Hz), 1.19_1.35 (10H, m), 1.47 (2H, m), 2.23 (2H, m), 2.49 (1H, brs), 3.39 (4H, t, J=5.4 Hz), 3.70-3.88 (4H, m), 6.25 (1H, d, J=15.0 Hz), 6.67 (2H, d, J=6.4 Hz), 6.95 (1H, dt, J=15.0, 7.3 Hz), 8.31 (2H, d, J=6.4 Hz)

Example 30

Production of 1-((E)-2-Decenoyl)-4-(pyridin-2-yl)piperazine [Compound 30]

The same procedures as in Example 1 were carried out using (E)-2-decenoic acid and 1-(2-pyridyl)piperazine as starting raw materials, to produce an intended compound.

Colorless crystals, mp 59°-61° C., $C_{19}H_{29}N_3O$ MW 315, HR-ESIMS (positive ion mode): m/z 316.2346 [M+H]$^+$ (Calcd for $C_{19}H_{29}N_3O$, 316.2383), $^1$H-NMR (400 MHz, CDCl$_3$) δ: 0.88 (3H, t, J=7.2 Hz), 1.22-1.35 (8H, m), 1.47 (2H, m), 2.22 (2H, m), 3.53 (2H, brs), 3.60-3.71 (4H, m), 3.81 (2H, brs), 6.27 (1H, d, J=15.2 Hz), 6.64-6.69 (2H, t, m), 6.93 (1H, dt, J=15.2, 7.3 Hz), 7.51 (1H, m), 8.20 (1H, m)

Example 31

Production of 1-((E)-2-Decenoyl)-4-(pyrimidin-2-yl)piperazine [Compound 31]

The same procedures as in Example 1 were carried out using (E)-2-decenoic acid and 1-(2-pyrimidyl)piperazine as starting raw materials, to produce an intended compound.

Colorless crystals, mp 93°-94° C., $C_{18}H_{28}N_4O$ MW 316, HR-ESIMS (positive ion mode): m/z 339.2155 [M+Na]$^+$ (Calcd for $C_{18}H_{29}N_4ONa$, 339.2161), $^1$H-NMR (400 MHz, CDCl$_3$) δ: 0.88 (3H, t, J=7.2 Hz), 1.22-1.35 (8H, m), 1.47 (2H, m), 2.23 (2H, m), 3.64 (2H, brs), 3.76 (2H, brs), 3.82-3.88 (4H, m), 6.28 (1H, d, J=15.2 Hz), 6.54 (1H, t, J=4.9 Hz), 6.93 (1H, dt, J=15.2, 7.4 Hz), 8.33 (2H, d, J=4.9 Hz).

Example 32

Production of 1-((E)-2-Decenoyl)azepane [Compound 32]

The same procedures as in Example 1 were carried out using (E)-2-decenoic acid and hexamethyleneimine as starting raw materials, to produce an intended compound.

Pale brown oily substance, $C_{16}H_{29}NO$ MW 251, HR-ESIMS (positive ion mode): m/z 274.2145 [M+Na]$^+$ (Calcd for $C_{16}H_{29}NONa$, 274.2147), $^1$H-NMR (400 MHz, CDCl$_3$) δ: 0.88 (3H, t, J=6.8 Hz), 1.24-1.33 (8H, m 1.45 (2H, m), 1.53-1.60 (4H, m), 1.69-1.77 (4H, m), 2.20 (2H, m), 3.50 (2H, t, J=6.0 Hz), 3.58 (2H, t, J=6.2 Hz), 6.22 (1H, d, J=15.6 Hz), 6.90 (1H, dt, J=15.6, 7.4 Hz).

Example 33

Production of 1-((E)-2-Decenoyl)-4-methyl-[1,4]diazepane [Compound 33]

The same procedures as in Example 2 were carried out using (E)-2-decenoic acid and 1-methyl-1,4-diazepane as starting raw materials, to produce an intended compound.

Pale yellow oily substance, $C_{16}H_{30}N_2O$ MW 266.4, EIMS:

m/z 267 [M+H]$^+$, $^1$H-NMR (500 MHz, DMSO-d$_6$) δ: 0.86 (t, J=7.0 Hz, 3H), 1.19-1.31 (m, 8H), 1.36-1.45 (m, 2H), 1.71-1.81 (m, 2H), 2.13-2.20 (m, 2H), 2.23 and 2.24 (s×2, 3H), 2.39-2.55 (m, 4H), 3.46-3.58 (m, 4H), 6.34-6.40 (m, 1H), 6.61-6.69 (m, 1H).

Example 34

Production of 1-((E)-2-Decenoyl)-4-(2-dimethylaminoethyl)-[1,4]diazepane [Compound 34]

The same procedures as in Example 2 were carried out using (E)-2-decenoic acid and 1-(2-dimethylaminoethyl)-1,4-diazepane as starting raw materials, to produce an intended compound.

Pale yellow oily substance, $C_{19}H_{37}N_3O$ MW 323.5, EIMS:

m/z 324 [M+H]$^+$, $^1$H-NMR (500 MHz, DMSO-d$_6$) δ: 0.86 (t, J=7.0 Hz, 3H), 1.20-1.30 (m, 8H), 1.36-1.44 (m, 2H), 1.67-1.75 (m, 2H), 2.11 (s, 6H), 2.13-2.20 (m, 2H), 2.26-2.31 (m, 2H), 2.48-2.59 (m, 4H), 2.60-2.67 (m, 2H), 3.44-3.57 (m, 4H), 6.33-6.40 (m, 1H), 6.60-6.69 (m, 1H).

Example 35

Production of 2-(1-((E)-2-Decenoyl)-4-piperidyl)acetic acid [Compound 35]

(1) The same procedures as in Example 2 were carried out using (E)-2-decenoic acid and ethyl 2-(4-piperidyl)acetate hydrochloride as starting raw materials, to produce ethyl 2-(1(E)-2-decenoyl)-4-piperidyl)acetate (ethyl ester of Compound 35).

(2) The ethyl 2-(1-((E)-2-decenoyl)-4-piperidyl)acetate was subjected to alkali saponification in the same manner as in Example 3, to produce an intended compound.

White crystals, mp 65°-66° C., $C_{17}H_{29}NO_3$ MW 295.4, EIMS: m/z 296[M+H]$^+$, $^1$H-NMR (500 MHz, DMSO-d$_6$) δ: 0.87 (t, J=7.1 Hz, 3H), 0.96-1.10 (m, 2H), 1.20-1.31 (m, 8H), 1.36-1.43 (m, 2H), 1.63-1.72 (m, 2H), 1.85-1.94 (m, 1H), 2.11-2.18 (m, 4H), 2.53-2.62 (m, 1H), 2.95-3.05 (m, 1H), 3.98-4.05 (m, 1H), 4.32-4.41 (m, 1H), 6.43 (d, J=15.0 Hz, 1G), 6.61 (dt, Jd=15.0 Hz, Jt=7.0 Hz, 1H).

Example 36

Production of 3-(1((E)-2-Decenoyl)-4-piperidyl)propanoic acid [Compound 36]

(1) The same procedures as in Example 2 were carried out using (E)-2-decenoic acid and ethyl 3-(4-piperidyl)propionate hydrochloride as starting raw materials, to produce ethyl 3-(1-((E)-2-decenoyl)-4-piperidyl)propionate (ethyl ester of Compound 36).

(2) The ethyl 3-(1-((E)-2-decenoyl)-4-piperidyl)propionate was subjected to alkali saponification in the same manner as in Example 3, to produce an intended compound.

Colorless oily substance, $C_{18}H_{31}NO_3$ MW 309.4, EIMS: m/z 310 [M+H]$^+$, $^1$H-NMR (500 MHz, DMSO-d$_6$) δ: 0.86 (t, J=6.5 Hz, 3H), 0.90-1.02 (m, 2H), 1.20-1.31 (m, 8H), 1.36-1.51 (m, 5H), 1.63-1.71 (m, 2H), 2.132.18 (m, 2H), 2.23 (t, J=7.5 Hz, 2H), 2.50-2.58 (m, 1H), 2.90-3.00 (m, 1H), 3.98-4.06 (m, 1H), 4.35-4.43 (m, 1H), 6.43 (d, J=15.0 Hz, 1H), 6.61 (dt, Jd=15.0 Hz, Jt=7.0 Hz, 1H), 12.03 (br, 1H).

Example 37

Production of 1-((E)-2-Decenoyl)-4-cyanopiperidine [Compound 37]

The same procedures as in Example 2 were carried out using (E)-2-decenoic acid and piperidine-4-carbonitrile as starting raw materials, to produce an intended compound.

Colorless oily substance, $C_{16}H_{26}N_2O$ MW 262.4, EIMS: m/z 263 [M+H]$^+$, $^1$H-NMR (500 MHz, DMSO-d$_6$) δ: 0.87 (t, J=6.5 Hz, 3H), 1.20-1.23 (m, 8H), 1.37-1.43 (m, 2H), 1.56-1.69 (m, 2H), 1.81-1.90 (m, 2H), 2.14-2.19 (m, 2H), 3.08-3.14 (m, 1H), 3.20-3.28 (m, 1H), 3.35-3.43 (m, 1H), 3.70-3.83 (m, 2H), 6.45 (d, J=15.0 Hz, 1H), 6.65 (dt, Jd=15.0 Hz, Jt=7.0 Hz, 1H).

Example 38

Production of 1((E)-2-Decenoyl)-4-(4-chlorophenyl)piperidine [Compound 38]

The same procedures as in Example 2 were carried out using (E)-2-decenoic acid and 4-(4-chlorophenyl)piperidine as starting raw materials, to produce an intended compound.

Pale yellow oily substance, $C_{21}H_{30}ClNO$ MW 347.9, EIMS: m/z 348 [M+H]$^+$, $^1$H-NMR (500 MHz, DMSO-d$_6$) δ: 0.86 (t, J=7.0 Hz, 3H), 1.22-1.32 (m, 8H), 1.32-1.54 (m, 4H), 1.74-1.83 (m, 2H), 2.15-2.21 (m, 2H), 2.26-2.69 (m, 1H), 2.75-2.83 (m, 1H), 3.05-3.15 (m, 1H), 4.12-4.21 (m, 1H), 4.54-4.62 (m, 1H), 6.48 (d, J=15.0 Hz, 1H), 6.65 (dt, Jd=15.0 Hz, Jt=7.0 Hz, 1H), 7.27 (d, J=8.5 Hz, 2H), 7.34 (d, J=8.5 Hz, 2H).

Example 39

Production of [4-[(E)-2-Decenoyl]piperazin-1-yl]acetic acid hydrochloride [Compound 39]

(1) The same procedures as in Example 2 were carried out using (E)-2-decenoic acid and ethyl 2-(1-piperazinyl)acetate dihydrochloride as starting raw materials, to produce ethyl [4-[(E)-2-decenoyl)piperazin-1-yl]acetate (ethyl ester of a free form of Compound 39).

(2) The ethyl [4-[(E)-2-decenoyl)piperazin-1-yl]acetate was subjected to alkali saponification in the same manner as in Example 3, to produce [4-[(E)-2-decenoyl)piperazin-1-yl]acetic acid (a free form of Compound 39).

(3) The compound obtained was dissolved in methylene chloride, and then treated with hydrogen chloride-dioxane, to produce an intended compound.

White crystals, mp 195° C. (decomposition), $C_{16}H_{29}ClN_2O_3$ MW 332.9, EIMS: m/z 297 [M+H]$^+$, $^1$H-NMR (500 MHz, DMSO-d$_6$) δ: 0.87 (t, J=7.0 Hz, 3H), 1.20-1.33 (m, 8H), 1.38-1.46 (m, 2H), 2.15-2.21 (m, 2H), 3.20-3.53 (m, 4H), 3.70-4.10 (m, 4H), 4.12 (s, 2H), 6.48 (d, J=15.0 Hz, 6.73 (dt, Jd=15.0 Hz, Jt=7.0 Hz, 1H).

Example 40

Production of 4-[4-[(E)-2-Decenoyl]piperazin-1-yl]butanoic acid hydrochloride [Compound 40]

(1) The same procedures as in Example 2 were carried out using (E)-2-decenoic acid and ethyl 4-(1-piperazinyl)butyrate dihydrochloride as starting raw materials, to produce ethyl 4-[4-((E)-2-decenoyl)piperazin-1-yl)butanoate (ethyl ester of a free form of Compound 40).

(2) The ethyl 4-[4-((E)-2-decenoyl)piperazin-1-yl)butanoate was subjected to alkali saponification in the same manner as in Example 3, to produce 4-[4-[(E)-2-decenoyl)piperazin-1-yl]butanoic acid (a free form of Compound 40).

(3) The compound obtained was dissolved in methylene chloride, and then treated with hydrogen chloride-dioxane, to produce an intended compound.

White crystals, mp 203°-205° C., $C_{18}H_{33}ClN_2O_3$ MW 360.9, EIMS: m/z 325 [M+H]$^+$, $^1$H-NMR (500 MHz, DMSO-d$_6$) δ: 0.86 (t, J=7.0 Hz, 3H), 1.20-1.31 (m, 8H), 1.35-1.43 (m, 2H), 1.61-1.69 (m, 2H), 2.13-2.18 (m, 2H), 2.23 (t, J=7.2 Hz, 2H), 2.26-2.35 (m, 6H), 3.45-3.55 (m, 4H), 6.43 (d, J=15.0 Hz, 1H), 6.64 (dt, Jd=15.0 Hz, Jt=7.0 Hz, 1H).

Example 41

Production of 1-((E)-2-Decenoyl)-4-(4-chlorophenyl)piperazine [Compound 41]

The same procedures as in Example 2 were carried out using (E)-2-decenoic acid and 1-(4-chlorophenyl)piperazine as starting raw materials, to produce an intended compound.

Pale yellow oily substance, $C_{20}H_{29}ClN_2O$ MW 348.9, EIMS: m/z 348 [M]$^+$, $^1$H-NMR (500 MHz, DMSO-d$_6$) δ: 0.86 (t, J=6.5 Hz, 3H), 1.20-1.31 (m, 8H), 1.37-1.45 (m, 2H), 2.15-2.22 (m, 2H), 3.07-3.18 (m, 4H), 3.60-3.70 (m, 4H), 6.51 (d, J=15.0 Hz, 1H), 6.70 (dt, Jd=15.0 Hz, Jt=7.0 Hz, 1H), 6.90 (d, J=9.0 Hz, 2H), 7.25 (J =9.0 Hz, 2H).

Example 42

Production of 1-((E)-2-Decenoyl)-4-(4-methoxyphenyl)piperazine [Compound 42]

The same procedures as in Example 2 were carried out using (E)-2-decenoic acid and 1-(4-methoxyphenyl)piperazine as starting raw materials, to produce an intended compound.

White crystals, mp 50°-52° C., $C_{21}H_{32}N_2O_2$ MW 344.5, EIMS: m/z 344 [M]$^+$, $^1$H-NMR (500 MHz, DMSO-d$_6$) δ: 0.86 (t, J=6.8 Hz, 3H), 1.20-1.31 (m, 8H), 1.38-1.45 (m, 2H), 2.15-2.21 (m, 2H), 2.94-3.01 (m, 4H), 3.60-3.67 (m, 4H), 3.68 (s, 3H), 6.50 (d, J =15.0 Hz, 1H), 6.68 (dt, Jd=15.0 Hz, Jt=7.0 Hz, 1H), 6.83 (d, J=9.1 Hz, 2H), 6.91 (d, J =9.1 Hz, 2H).

Example 43

Production of 1-((E)-2-Decenoyl)-4-(4-methylphenyl)piperazine [Compound 43]

The same procedures as in Example 2 were carried out using (E)-2-decenoic acid and 1-(p-tolyl)piperazine as starting raw materials, to produce an intended compound.

White crystals, mp 45°-46° C., $C_{21}H_{32}N_2O$ MW 328.5, EIMS: m/z 328 [M]$^+$, $^1$H-NMR (500 MHz, DMSO-d$_6$) δ: 0.85 (t, J=6.9 Hz, 3H), 1.20-1.30 (m, 8H), 1.36-1.45 (m, 2H), 2.20 (s, 3H), 2.15-2.23 (m, 2H), 3.00-3.08 (m, 4H), 3.60-3.70 (m, 4H), 6.50 (d, J =15.0 Hz, 1H), 6.69 (dt, Jd=15.0 Hz, Jt=7.0 Hz, 1H), 6.85 (d, J=8.5 Hz, 2H), 7.03 (d, J =8.5 Hz, 2H).

Example 44

Production of 1-((E)-2-Decenoyl)-4-(4-fluorophenyl)piperazine [Compound 44]

The same procedures as in Example 2 were carried out using (E)-2-decenoic acid and 1-(4-fluorophenyl)piperazine as starting raw materials, to produce an intended compound.

Pale yellow oily substance, $C_{20}H_{29}FN_2O$ MW 332.5, EIMS: m/z 332 [M]$^+$, $^1$H-NMR (500 MHz, DMSO-d$_6$) δ: 0.86 (t, J=6.5 Hz, 3H), 1.20-1.31 (m, 8H), 1.37-1.45 (m, 2H), 2.16-2.22 (m, 2H), 3.00-3.09 (m, 4H), 3.62-3.72 (m, 4H), 6.50 (d, J=15.0 Hz, 1H), 6.69 (dt, Jd=15.0 Hz, Jt=7.0 Hz, 1H), 6.95-7.00 (m, 2H), 7.03-7.09 (m, 2H).

Example 45

Production of 1-((E)-2-Decenoyl)-4-(2-chlorophenyl)piperazine [Compound 45]

The same procedures as in Example 2 were carried out using (E)-2-decenoic acid and 1-(2-chlorophenyl)piperazine as starting raw materials, to produce an intended compound.

Pale yellow oily substance, $C_{20}H_{29}ClN_2O$ MW 348.9, EIMS: m/z 348 [M]$^+$, $^1$H-NMR (500 MHz, DMSO-d$_6$) δ: 0.86 (t, J=6.5 Hz, 3H), 1.21-1.31 (m, 8H), 1.38-1.45 (m, 2H), 2.15-2.21 (m, 2H), 2.90-2.98 (m, 4H), 3.65-3.75 (m, 4H), 6.50 (d, J=15.0 Hz, 1H), 6.70 (dt, Jd=15.0 Hz, Jt=7.0 Hz, 1H), 7.04-7.08 (m, 1H), 7.13-7.17 (m, 1H), 7.28-7.32 (m, 1H), 7.41-7.45 (m, 1H).

Example 46

Production of 1-((E)-2-Decenoyl)-4-(4-hydroxyphenyl)piperazine [Compound 46]

The same procedures as in Example 2 were carried out using (E)-2-decenoic acid and 4-(1-piperazinyl)phenol as starting raw materials, to produce an intended compound.

Pale red crystals, mp 85°-87° C., $C_{20}H_{30}N_2O_2$ MW 330.5, EIMS: m/z 330 [M+H]$^+$, $^1$H-NMR (500 MHz, DMSO-d$_6$) δ: 0.86 (t, J=7.0 Hz, 3H), 1.20-1.30 (m, 8H), 1.38-1.40 (m, 2H), 2.15-2.21 (m, 2H), 2.87-2.96 (m, 4H), 3.59-3.69 (m, 4H), 6.49 (d, J=15.0 Hz, 1H), 6.63-6.71 (m, 3H), 6.80 (d, J=6.8 Hz, 2H), 8.88 (s, 1H).

Example 47

Production of 2-[4-[4-((E)-2-Decenoyl)piperazin-1-yl]phenoxy]acetic acid [Compound 47]

(1) The same procedures as in Example 2 were carried out using (E)-2-decenoic acid and ethyl 2-[4-(1-piperazinyl)phenoxy]acetate dihydrochloride as starting raw materials, to produce ethyl 2-[4-[4-((E)-2-decenoyl)piperazin-1-yl]phenoxy]acetate (ethyl ester of Compound 47).

(2) The ethyl 2-[4-[4-((E)-2-decenoyl)piperazin-1-yl]phenoxy]acetate was subjected to alkali saponification in the same manner as in Example 3, to produce an intended compound.

White crystals, mp 210° C. (decomposition), $C_{22}H_{32}N_2O_4$ MW 388.5, EIMS: m/z 388 [M]$^+$, $^1$H-NMR (500 MHz, DMSO-d$_6$) δ: 0.86 (t, J=7.0 Hz, 3H), 1.21-1.32 (m, 8H), 1.37-1.45 (m, 2H), 2.15-2.20 (m, 2H), 2.91-3.00 (m, 4H), 3.60-3.71 (m, 4H), 6.50 (d, J=15.0 Hz, 1H), 6.68 (dt, Jd=15.0 Hz, Jt=7.0 Hz, 1H), 6.76 (d, J=7.1 Hz, 2H), 6.87 (d, J=7.1 Hz, 2H).

Example 48

Production of 4-[[4-((E)-2-Decenoyl)piperazin-1-yl]methyl]benzoic acid [Compound 48]

(1) The same procedures as in Example 2 were carried out using (E)-2-decenoic acid and methyl 4-[1-piperazinylmethyl)benzoate dihydrochloride as starting raw materials, to produce methyl 4[[4-((E)-2-decenoyl)piperazin-1-yl]methyl]benzoate (methyl ester of Compound 48).

(2) The methyl 4-[[4-((E)-2-decenoyl)piperazin-1-yl]methyl]benzoate was subjected to alkali saponification in the same manner as in Example 3, to produce an intended compound.

White crystals, mp 114°-116° C., $C_{22}H_{32}N_2O_3$ MW 372.5, EIMS: m/z 373 [M+H]$^+$, $^1$H-NMR (500 MHz, DMSO-d$_6$) δ: 0.86 (t, J=7.0 Hz, 3H), 1.20-1.30 (m, 8H), 1.35-1.43 (m, 2H), 2.12-2.18 (m, 2H), 2.30-2.38 (m, 4H), 3.45-3.55 (m, 4H), 3.55 (s, sH), 6.43 (d, J =15.0 Hz, 1H), 6.64 (dt, Jd=15.0 Hz, Jt=7.0 Hz, 1H), 7.44 (d, J=8.2 Hz, 2H), 12.8 (br, 1H).

Example 49

Production of 4-[(E)-2-Decenoyl]morpholine-3-carboxylic acid [Compound 49]

(1) The same procedures as in Example 2 were carried out using (E)-2-decenoic acid and methyl morpholine-3-carboxylate hydrochloride as starting raw materials, to produce methyl 4-[(E)-2-decenoyl)morpholine-3-carboxylate (methyl ester of Compound 49).

(2) The methyl 4-[(E)-2-decenoyl)morpholine-3-carboxylate was subjected to alkali saponification in the same manner as in Example 3, to produce an intended compound.

Pale yellow oily substance, $C_{15}H_{25}NO_4$ MW 283.4, EIMS: m/z 284 [M+H]$^+$, $^1$H-NMR (500 MHz, CDCl$_3$) δ: 0.88 (t, J=7.0 Hz, 3H), 1.22-1.35 (m, 8H), 1.40-1.50 (m, 2H), 2.17-2.26 (m, 2H), 3.10-4.00 (m, 5H), 4.45-4.40 and 5.15-5.18 (m, 2H), 6.05 and 6.23 (d x 2, J =15.0 Hz, 1H), 6.88-7.02 (m, 1H), 9.00 (br, 1H).

Test Example 1

Evaluation for Action Against Rat Peripheral Nerve Disorder Induced by Paclitaxel The effects of the compounds of the present invention were evaluated for a peripheral nerve disorder which is a side effect induced by the administration of an anti-cancer agent paclitaxel, such as hyperesthesia including allodynia induced by mechanical stimuli, which is a severe pain induced by such tactile stimuli which usually cause no pains. The compound of the present invention was intraperitoneally administered to rats as a test drug to conduct a von Frey test.

(1) Preparation of Rats with Paclitaxel-Induced Peripheral Nerve Disorder and Administration of Test Drugs Male SD rats of six weeks age (six rats per group) were used as experimental animals, and paclitaxel (2 mg/kg) was intraperitoneally administered every other day for four times in total to prepare rats with paclitaxel-induced peripheral nerve disorder. During the period of 18 to 25 days or during the period of 20 to 27 days after the initiation of paclitaxel administration, the test drug was intraperitoneally administered in a single dose of 300 μ/kg, and the following von Frey test was conducted.

(2) von Frey Test

The rats of the above (1) were placed in a transparent acrylic cage with a wire-meshed floor and habituated for about three minutes, and the 50% reaction threshold values to the mechanical stimulus of right hind limb were measured before administration of the test drug and after 1 and 5 hours from the initiation of the administration.

The measurement was conducted using von Frey filaments (manufactured by North Coast Medical Inc.) in accordance with the methods of Chaplan, et al. (*Journal of Neuroscience Methods*, 53(1), 55-63, 1994) and Dixon, et al. (*Annual Review of Pharmacology and Toxicology*, 20, 441-462, 1980). Of eight filaments [stimulus loads (g): 0.4, 0.6, 1.0, 2.0, 4.0, 6.0, 8.0 and 15.0], the test was started as from the filament of 2.0 g, the filament was vertically attached to the sole for 2 to 3 seconds with such a force that the filament was lightly bent and the case where the hind limb showed an escape reaction was called a positive reaction. The case where the rat escaped at the instance of removing the filament was also called positive. When the positive reaction was found, stimulus was applied similarly with a filament of one rank weaker, and in the absence of the reaction, stimulus was similarly applied with a filament of one rank stronger, and a point where the reaction changed from negative to positive or from positive to negative was called the first two reactions. Subsequently, stimuli were applied for continuously four times by the same up-down method. A 50% reaction threshold value to the mechanical stimulus was measured using the reaction to the six stimuli in total and then (mean value)±(standard error) for each group was calculated. Incidentally, when stimulus reached to a load of 15.0 g without positive reaction, or when positive reaction continued to a load of 0.4 g, 15.0 g or 0.25 g was adopted as each of 50% reaction threshold values. With regard to the higher 50% reaction threshold value between the 50% threshold values after 1 hour and 5 hours from administration of a test drug, a recovery rate (%) of the 50% reaction threshold value was calculated by the following expression in which 15 was taken as a normal threshold value. One example of the above test results is shown in Tables 6 and 7.

Recovery rate (%) of 50% reaction threshold value= [(50% reaction threshold value after 1 hour or 5 hours from administration of test drug)−(50% reaction threshold value before administration of test drug)]/[(Normal threshold value)−(50% reaction threshold value before administration of test drug)]×100

TABLE 6

| Test Drug | Recovery Rate of 50% Reaction Threshold Value (%) |
|---|---|
| Compound 1 | 58.2 |
| Compound 2 | 23.5 |
| Compound 4 | 43.7 |
| Compound 5 | 41.6 |
| Compound 6 | 33.8 |
| Compound 7 | 45.2 |
| Compound 8 | 49.7 |
| Compound 9 | 35.6 |
| Compound 10 | 44.6 |
| Compound 12 | 49.7 |
| Compound 13 | 23.2 |
| Compound 14 | 26.0 |
| Compound 15 | 34.2 |
| Compound 16 | 38.6 |
| Compound 17 | 30.6 |
| Compound 18 | 48.9 |
| Compound 19 | 19.8 |
| Compound 20 | 26.9 |
| Compound 21 | 34.8 |
| Compound 22 | 29.7 |
| Compound 23 | 33.0 |
| Compound 24 | 49.7 |
| Compound 25 | 55.3 |
| Compound 26 | 24.1 |
| Compound 27 | 69.1 |
| Compound 28 | 20.3 |
| Compound 29 | 42.8 |
| Compound 30 | 22.6 |
| Compound 31 | 22.9 |
| Compound 32 | 51.1 |
| Compound 33 | 33.4 |
| Compound 34 | 35.5 |

TABLE 7

| Test Drug | Recovery Rate of 50% Reaction Threshold Value (%) |
|---|---|
| Compound 35 | 41.2 |
| Compound 36 | 42.0 |
| Compound 37 | 22.4 |
| Compound 38 | 55.5 |
| Compound 39 | 16.6 |
| Compound 40 | 61.6 |
| Compound 41 | 81.5 |
| Compound 42 | 45.8 |
| Compound 43 | 31.3 |
| Compound 44 | 42.6 |
| Compound 45 | 33.3 |
| Compound 46 | 53.7 |
| Compound 47 | 54.5 |
| Compound 48 | 56.4 |

Tables 6 and 7 show that the compounds of the present invention exhibits an excellent improving effect for hyperesthesia induced by administration of paclitaxel, and thus have an alleviating action for the side effects induced by administration of an anti-cancer agent. In addition, the compounds of the present invention also show an excellent improving action to hyperesthesia when oxaliplatin of platinum drugs, is used in the same manner as that when paclitaxel of taxane drugs is used.

Test Example 2

Evaluation of Activation (Phosphorylation) of MAP Kinase

With regard to the compounds of the present invention, the activation of MAP kinase (ERK 1/2) was measured in accordance with a Western immunoblotting in the following manner.

Nerve cells were dispersed from cerebral cortex of a fetal rat of 17 days age, and the nerve cells were cultured for one day in a Dulbecco's modified Eagle's medium (DMEM) containing 5% fetal bovine serum. The culture medium was exchanged with a serum-free medium (B27 supplemented Neurobasal; Invitrogen), and the nerve cells were cultured at the density of 20,000 to 40,000 cells/$cm^2$ in a polyornithine-coated culture dish.

After three days, the compound of the present invention was added, and the culture was continued for 30 minutes. Thereafter, the cells were recovered on ice using a solution containing a phosphatase inhibitor where Tris-HCl buffer was used as a base. The protein concentration of the resulting cell extract was quantified with a BCA Protein Assay Kit (Takara Bio Co., Ltd.), and a certain amount of the protein (3 μg for the measurement of MAP kinase and 5 μg for the measurement of phosphorylated MAP kinase) was subjected to polyacrylamide gel electrophoresis. The protein was transferred from the electrophoresed gel to a PVDF membrane, and Western immunoblotting was carried out using each of an anti-MAP kinase antibody (Cell Signaling Technology) and an anti-phosphorylated MAP kinase antibody (Cell Signaling Technology) of the primary antibody.

Subsequently, the reaction with an alkaline phosphatase-labeled anti-rabbit IgG antibody (Promega) of the secondary antibody was carried out, and the enzymatic activity was allowed to develop color, to measure MAP kinase (MAPK) and the phosphorylated MAP kinase (pMAPK).

Incidentally, each of the compounds of the present invention was dissolved in 0.1% DMSO to adjust its concentration to 250 μg/ml. As to the control, 0.1% DMSO was added.

The intensity of the concentration of the bands of eletrophoresed the gel was calculated and quantified using Image J (K. K. Bioarts). The numerical values for the MAPK when using the compounds of the present invention were each divided by the numerical value for the MAPK of the control, and the numerical values for the pMAPK when using the compounds of the present invention were divided by the numerical value for the pMAPK of the control, whereby a ratio of the MAPK when using each of the compounds of the present invention to the control, and a ratio of the pMAPK when using each of the compounds of the present invention to the control were obtained. Subsequently, the ratio of the pMAPK to the control obtained was divided by the ratio of the MAPK to the control to obtain a ratio of the pMAPK to the MAPK. One example of the results are shown in Tables 8 to 10.

TABLE 8

| | Ratio of pMAPK to MAPK |
|---|---|
| Control | 1.00 |
| Compound 4 | 1.47 |
| Compound 7 | 1.62 |
| Compound 18 | 1.28 |

TABLE 9

| | Ratio of pMAPK to MAPK |
|---|---|
| Control | 1.00 |
| Compound 6 | 1.71 |
| Compound 14 | 2.08 |
| Compound 20 | 1.27 |
| Compound 23 | 1.30 |
| Compound 24 | 2.58 |

TABLE 10

| | Ratio of pMAPK to MAPK |
|---|---|
| Control | 1.00 |
| Compound 2 | 1.28 |
| Compound 13 | 1.63 |
| Compound 21 | 1.54 |
| Compound 26 | 1.48 |
| Compound 27 | 1.44 |

Tables 8 to 10 show that the compounds of the present invention show high activation (phosphorylation) of the MAP kinase, as compared to the control, suggesting to have a neurotrophic factor-like activity.

Test Example 3

Evaluation of Activation (Phosphorylation) of MAP Kinase Under Mild Stress Loads As to the compounds of the present invention, the activation level of the MAP kinase (ERK1/2) was measured using chronic mild stress-induced depression model mice in the following manner.

(1) Preparation of Chronic Mild Stress-Induced Depression Model Mice and Administration of Test Drug Female ddY mice of seven weeks age (n=8 to 12) were subjected to the following procedures: (A) The mice were subjected to forced swimming for 15 minutes, and then to normal breeding for two days. (B) The mice were subjected to breeding in an inclined cage for two days, and then to normal breeding for one day. (C) The mice were subjected to breeding for one day in a cage of which floor mat was made wet and then to normal breeding for one day. (D) The mice were subjected to breeding for one day with a cage rotating at a rate of 180 rotations/minute, and then to normal breeding for one day. Further, after one cycle of (A) to (D) was carried out, (B) to (D) were repeated for two cycles. As such, stress was applied over three weeks in total to prepare chronic mild stress-induced depression model mice. During that time, the compounds of the present invention each dissolved in PBS or in a PBS solvent containing DMSO, etc. were orally administered once every day over a period of three weeks.

(2) Measurements of MAP Kinase and Phosphorylated MAP Kinase

After the termination of the behavioral analyses after the above chronic mild stress loads (tail suspension test and light-darkness test), hippocampus was excised from the brain. The hippocampus and a disruption (20 mM Tris-HCl buffer (pH 7.4): RIPA buffer containing 1% Nonidet P40 [registered trademark], 1% sodium deoxycholate, 2 mM EDTA, 0.1% sodium dodecyl sulfate (SDS), 0.15 M NaCl, 10 mg/mL aprotinin, 10 mg/mL leupeptin, 50 mM NaF, 1 mM sodium orthovanadate, 1 mM phenylmethylsulfonyl fluoride (PMSF)) in an amount 19 times the wet weight of the hippocampus were placed in a microtube (1.5 mL), and the mixture was sonically disrupted. Thereafter, the microtube was allowed to stand on ice for 30 minutes, centrifuged at 1400×g for 15 minutes, to provide the supernatant as a protein extract. To the protein extract were added a sample buffer for electrophoresis (0.2 M Tris-HCl buffer (pH 7.2), 8% SDS, 40% glycerol, bromophenol blue (BPB)) in an amount ⅓ that of the protein extract, and 2-mercaptoethanol in an amount 1/10 that of the protein extract. The mixture was heat-treated at 95° C. for 5 minutes, and subjected to SDS electrophoresis with 10% polyacrylamide gel.

Each of the MAP kinase (MAPK) and the phosphorylated MAP kinase (pMAPK) was subjected to immunoblot analysis, and 2 µg or 5 µg each of tissue-extracted proteins was subjected to electrophoresis. Thereafter, the protein was transferred from the gel to a PVDF membrane. The transferred PVDF membrane was blocked with a solution containing 5% skim milk, and allowed to react with each of 1,000-fold dilutions of an anti-MAPK antibody and an anti-pMAPK antibody overnight at 4° C. Next, the reaction mixture was allowed to react with a secondary antibody (alkali phosphatase-labeled anti-mouse IgG antibody (5,000-fold dilution)), and finally incubated in a solution supplemented with a substrate of the alkali phosphatase for several minutes to allow color development. The staining intensity of each band was quantified, and a ratio of pMAPK to MAPK was obtained (n=4 to 7). Here, the significance test was conducted in accordance with Dunnett's test.

As a result of the above test, the ratio of pMAPK to MAPK of the normal animal control group was 1.26±0.11, and the same ratio of the mild stress-loaded animal control group was significantly lowered to 0.56±0.04. The same ratios in the group administered with the compounds of the present invention were such that the group administered with Compound 10 (1,000 µg/kg) was 1.00±0.04, and that the group administered with Compound 12 (500 µg/kg) was 1.09±0.04, thereby showing that the compounds of the present invention significantly increased the phosphorylation of MAPK that was lowered in the mild stress-loaded animal control group, and suggesting to have a neurotrophic factor-like activity.

Test Example 4

Evaluation of Activation (Phosphorylation) of CREB Under Mild Stress Loads

With respect to the compounds of the present invention, the activation level of transcription factor CREB (a ratio of phosphorylated CREB (pCREB) to CREB), which plays a key role in the functions of nerve cells and memorization and learning abilities, of which signal transmission pathway is located downstream of MAPK (ERK 1/2) was measured using the chronic mild stress-induced depression model mice, in the same manner as in Test Example 3 mentioned above in accordance with Western blotting (n=3 to 8). However, the primary antibodies (anti-CREB antibody and anti-pCREB antibody) were allowed to react in 1,000-fold dilutions, and the secondary antibodies were allowed to react in 10,000-fold dilutions.

As a result of the above test, the ratio of pCREB to CREB of the normal animal control group was 0.95±0.09, and the same ratio of the mild stress-loaded animal control group was significantly lowered to 0.50±0.07. The same ratios in the group administered with the compounds of the present invention were such that the group administered with Compound 10 (1,000 μg/kg) was 0.94±0.10, and that the group administered with Compound 12 (500 μg/kg) was 1.08±0.14, thereby showing that the compounds of the present invention significantly increased the ratio of pCREB that was lowered in the mild stress-loaded animal control group in the same manner as the case of the phosphorylation of MAPK, and suggesting to have a neurotrophic factor-like activity.

Test Example 5

Evaluation of Suppressive Effects of Depression Symptoms Accompanying Mild Stress Loads The compounds of the present invention were administered as a test drug to the chronic mild stress-induced depression model mice of Test Example 3(1) mentioned above, and the model mice were then subjected to tail suspension test to evaluate suppressive effects of depression symptoms. Specifically, mice were gripped at a location 1 cm away from the tip end of the mouse tail with a hand, and kept at a height 10 cm from the floor. The observations were made for 6 minutes, and the length of the immobility time, serving as an index of depression symptoms, was measured. Here, the significance test was conducted in accordance with Dunnett's test.

As a result of the above-mentioned tail suspension test, the immobility time of the normal animal control group was 73.16±9.20 seconds, and the immobility time of the mild stress-loaded animal control was significantly extended to 157.01±11.97 seconds. The immobility time of the group administered with Compound 12 of the present invention at a dose of 500 μg/kg was 69.26±16.41 seconds, thereby significantly showing suppressive effects on depression symptoms. In addition, the immobility time of the group administered with Compound 10 of the present invention at a dose of 1,000 μg/kg was 96.03±25.24 seconds, so that some suppression of depression symptoms was found.

Test Example 6

Evaluation of Suppressive Effects of Anxiety Symptoms Accompanying Mild Stress Loads The compounds of the present invention were administered as a test drug to the chronic mild stress-induced depression model mice of Test Example 3(1) mentioned above, and the model mice were then subjected to light-dark test to evaluate suppressive effects of anxiety symptoms. Specifically, a wooden rectangular apparatus composed of a light chamber and a dark chamber having a height of 50 cm, a length of 50 cm, a width of 25 cm was used, a mouse was placed in a dark chamber and allowed to freely search, and then the number of times invading into a light chamber, and the time staying in the light chamber were recorded for 5 minutes. This test is a test for evaluating anxiety level of mouse utilizing its characteristic of the tendency of the mice of liking dark places, and less likely to stay in light places, but might invade into a light chamber from a searching behavior out of curiosity. Here, the significance test was carried out in accordance with Dunnett's test.

As a result of the above light-dark test, contrary to the staying time in the light chamber of the normal animal control group of 110.74±5.29 seconds, the staying time in the light chamber of the mild stress-loaded control group was significantly lowered to 74.72±4.09 seconds. The staying time in the light chamber of the group administered with Compound 12 of the present invention at a dose of 500 μg/kg was 108.70±12.06 seconds, showing significant suppressive effects of anxiety symptoms. In addition, the staying time in the light chamber of the group administered with Compound 10 of the present invention at a dose of 1,000 μg/kg was 107.05±8.29 seconds, so that inhibition of anxiety symptoms was found.

Test Example 7

Evaluation of Analgesic Action Against Osteoarthritis Model Rats

The following experiments were conducted for examining the analgesic action of the analgesic of the present invention using the osteoarthritis (OA) rats induced by sodium monoiodoacetate (MIA) which were model animals for OA.

(1) Preparation of MIA-Induced OA Rats

A 50% reaction threshold value to the mechanical stimulus of male Wistar rats of six weeks age was measured (the measurement method will be mentioned later), and a normal control group was selected. MIA prepared with saline was administered in a single dose of 300 μg/50 μL into the right knee joint of the rats except for the normal control group, while 50 μL of saline was administered into the left knee joint, whereby MIA-induced OA rats were prepared. To the normal control group, 50 μL of saline was administered into the joints of both the knees.

(2) Grouping

With regard to the male Wistar rats of six weeks age used as experimental animals except the normal control group, their 50% reaction threshold values to the mechanical stimulus (the measuring method will be mentioned later) and body weights were measured after 24 days from the administration of MIA mentioned in (1) and then 3 groups, i.e. a normal control group, an onset control group, and a test drug-administered group, six rats per group, were organized.

(3) Administration of Test Drug

A test drug solution (100 μg/mL) using each of the compounds of the present invention as a test drug was prepared using a phosphate buffered saline (PBS) containing 0.1 vol % dimethyl sulfoxide (DMSO).

Immediately after the grouping (after 14 days from the administration of MIA), a test drug solution was intraperitoneally administered in a single dose of 500 μg/kg to a test drug-administered group. Also, to the normal control group and the onset control group, PBS containing 0.1 vol % DMSO was intraperitoneally administered in a single dose.

(4) Results of the Measurements of 50% Reaction Threshold Values to Mechanical Stimulus (von Frey Test)

The von Frey test was conducted in the same manner as in Test Example 1 (2), and a recovery rate (%) of the 50% reaction threshold values against hyperalgesia of OA induced by the administration of MIA was calculated. One example of the results is shown in Table 11.

TABLE 11

| Test Drug | Recovery Rate of 50% Reaction Threshold (%) |
|---|---|
| Compound 1 | 24.2 |
| Compound 5 | 35.8 |
| Compound 22 | 13.2 |
| Compound 25 | 18.9 |

As is clear from Table 11, the compounds of the present invention showed suppressive effects against hyperalgesia of OA induced by the administration of MIA, thereby suggesting their usefulness as an analgesic.

INDUSTRIAL APPLICABILITY

As is clear from the above-mentioned pharmacological test results, it was found that the compounds of the present invention had excellent therapeutic effects against hyperalgesia against mechanical stimulus induced in rats by the administration of anti-cancer agent. Therefore, the compounds of the present invention are effective as an agent for preventing or treating peripheral nerve disorders induced by anti-cancer agents, such as such as paresthesia such as numbness of limb extremities of human and animals, and hyperalgesia such as pains, so that the compounds are very highly useful.

In addition, in the evaluations using the rat cerebral cortex-cultured nerve cells and the hippocampus of the chronic mild stress-induced depression model mice, the compounds showed excellent MAP kinase phosphorylation action and CREB phosphorylation action (neurotrophic factor-like activity). Further, in various tests using the chronic mild stress-induced depression model mice, actions of improving depression symptoms or anxiety symptoms were shown. Therefore, it is expected that the compounds of the present invention are useful as prophylactic or therapeutic agents for dementia, Alzheimer's disease, Parkinson's disease, diabetic neuropathy, depression, glaucoma, autistic disorder spectrum, or the like, and repairing agents for spinal cord injury.

In addition, the compounds of the present invention have excellent analgesic effects and suppressive effects for hyperalgesia, in the animal experiments using MIA-induced OA rats, which are OA models. Therefore, the compounds of the present invention are highly useful as prophylactic or therapeutic agent for various pain diseases, including, for example, pains induced by OA or the like.

The invention claimed is:

1. A trans-2-decenoic acid derivative represented by the following general formula (I') or a pharmaceutically acceptable salt thereof:

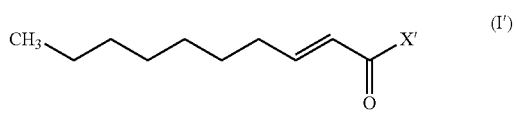

wherein X' is:
(a) a 1-pyrrolidyl substituted with carboxyl or alkoxycarbonyl,
(b) a 3-thiazolidyl,
(c) a piperidino substituted with oxo, hydroxy, alkoxy, carboxyl, alkoxycarbonyl, alkylamino, alkylaminoalkyl, phenyl, carboxyalkyl, alkoxycarbonylalkyl, cyano, or halogenophenyl,
(d) a thiomorpholino,
(e) a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl,
(f) a 1-piperazyl substituted with a phenyl which may be substituted with alkylamino, halogen, alkoxy, alkyl, hydroxy, carboxyalkoxy or alkoxycarbonylalkoxy,
(g) a 1,4-diazepanyl which may be substituted with alkyl or alkylaminoalkyl, or
(h) a carboxymorpholino.

2. The trans-2-decenoic acid derivative or a pharmaceutically acceptable salt thereof according to claim 1, wherein X' is a 1-pyrrolidyl substituted with carboxyl or alkoxycarbonyl.

3. The trans-2-decenoic acid derivative or a pharmaceutically acceptable salt thereof according to claim 1, wherein X' is a 3-thiazolidyl, a thiomorpholino or a carboxymorpholino.

4. The trans-2-decenoic acid derivative or a pharmaceutically acceptable salt thereof according to claim 1, wherein X' is a piperidino substituted with oxo, hydroxy, alkoxy, carboxyl, alkoxycarbonyl, alkylamino, alkylaminoalkyl, phenyl, carboxyalkyl, alkoxycarbonylalkyl, cyano or halogenophenyl.

5. The trans-2-decenoic acid derivative or a pharmaceutically acceptable salt thereof according to claim 1, wherein X' is a 1-piperazyl which may be substituted with alkyl, carboxyalkyl, alkoxycarbonylalkyl, alkylaminoalkyl, cycloalkyl, piperidinoalkyl, phenylalkyl, pyridyl, pyrimidyl, carboxyphenylalkyl or alkoxycarbonylphenylalkyl.

6. The trans-2-decenoic acid derivative or a pharmaceutically acceptable salt thereof according to claim 1, wherein X' is a 1-piperazyl substituted with a phenyl which may be substituted with alkylamino, halogen, alkoxy, alkyl, hydroxy, carboxyalkoxy or alkoxycarbonylalkoxy.

7. The trans-2-decenoic acid derivative or a pharmaceutically acceptable salt thereof according to claim 1, wherein X' is a 1,4-diazepanyl which may be substituted with alkyl or alkylaminoalkyl.

8. A pharmaceutical agent comprising, as an active ingredient, at least one trans-2-decenoic acid derivative or pharmaceutically acceptable salt thereof according to claim 1.

* * * * *